US007618952B2

(12) United States Patent
Ehrenfreund et al.

(10) Patent No.: US 7,618,952 B2
(45) Date of Patent: *Nov. 17, 2009

(54) SILICON COMPOUNDS WITH MICROBIOCIDAL ACTIVITY

(75) Inventors: Josef Ehrenfreund, Basel (CH); Clemens Lamberth, Basel (CH); Hans Tobler, Basel (CH); Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 417 days.

This patent is subject to a terminal disclaimer.

(21) Appl. No.: 10/569,343

(22) PCT Filed: Sep. 8, 2004

(86) PCT No.: PCT/EP2004/010009

§ 371 (c)(1),
(2), (4) Date: Feb. 21, 2006

(87) PCT Pub. No.: WO2005/028485

PCT Pub. Date: Mar. 31, 2005

(65) Prior Publication Data

US 2006/0287328 A1 Dec. 21, 2006

(30) Foreign Application Priority Data

Sep. 19, 2003 (GB) .................... 0322012.6

(51) Int. Cl.
*A61K 31/695* (2006.01)
*C07F 7/18* (2006.01)
*C07F 7/08* (2006.01)
*C07F 17/00* (2006.01)

(52) U.S. Cl. ............... 514/63; 556/9; 556/10; 556/11; 556/12

(58) Field of Classification Search ...... 556/9, 556/10, 11, 12; 514/63
See application file for complete search history.

(56) References Cited

U.S. PATENT DOCUMENTS

2006/0276434 A1* 12/2006 Ehrenfreund et al. ......... 514/63

FOREIGN PATENT DOCUMENTS

WO      WO 98/52944      11/1998

* cited by examiner

Primary Examiner—Alton N Pryor
(74) Attorney, Agent, or Firm—James Cueva

(57) ABSTRACT

Fungicidal compounds of formula (I): where X is O or S; RING is phenyl or thienyl; Het is a 5- or 6-membered heterocyclic ring containing one to three heteroatoms, each independently selected from oxygen, nitrogen and sulphur, the ring being substituted by one to four groups $R^4$; $R^1$ is hydrogen, optionally substituted $(C_{1-4})$alkyl, formyl, optionally substituted $(C_{1-4})$alkylC(=O), optionally substituted $(C_{1-4})$alkylC(=O)O, optionally substituted $(C_{1-4})$alkoxy$(C_{1-4})$alkyl, optionally substituted allyl, optionally substituted propargyl or optionally substituted allenyl; each $R^2$ is, independently, halogen, optionally substituted $(C_{1-4})$alkyl, optionally substituted $(C_{1-4})$alkoxy or optionally substituted $(C_{1-4})$alkoxy$(C_{1-4})$alkyl; $R^3$ is $(CR^aR^b)_m$—Cy—$(CR^cR^d)_n$—Y; each $R^4$ is, independently, selected from halogen, $C_{1-3}$ alkyl, $C_{1-3}$ haloalkyl, $C_{1-3}$alkoxy$(C_{1-3})$alkyl and cyano; $R^a$, $R^b$, $R^c$ and $R^d$ are each, independently, hydrogen or optionally substituted $(C_{1-4})$alkyl; Cy is an optionally substituted carbocyclic or heterocyclic 3-7 membered ring which may be saturated, unsaturated or aromatic and which optionally contains a silicon atom as a ring member; $(CR^aR^b)_m$ and $(CR^cR^d)_n$ may be bound either to the same carbon or silicon atom of Cy or to different atoms separated by 1, 2 or 3 ring members; Y is $Si(O_pZ^1)(O_qZ^2)(O_sZ)$ and provided that Cy contains a silicon atom as a ring member then Y may also be hydrogen; Z is $C_{1-4}$ alkyl or $C_{2-4}$ alkenyl (each of which is optionally interrupted by one heteroatom selected from O, S and N and is optionally substituted by one to three independently selected halogen atoms); $Z^1$ and $Z^2$ are, independently, methyl or ethyl; in and n are each, independently, 0, 1, 2 or 3; p, q and s are each, independently, 0 or 1; and r is 0, 1 or 2; or an N-oxide thereof; novel intermediates used in the preparation of these compounds, agrochemical compositions which comprise at least one of the novel compounds as active ingredient and the use of the active ingredients or compositions in agriculture or horticulture for controlling or preventing infestation of plants by phytopathogenic microorganisms, preferably fungi.

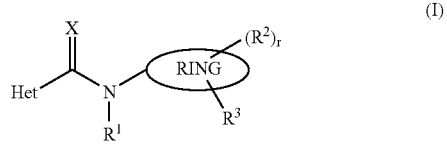

(I)

9 Claims, No Drawings

SILICON COMPOUNDS WITH MICROBIOCIDAL ACTIVITY

This application is a 371 of International Application No. PCT/EP2004/010009 filed Sep. 8, 2004, which claims priority to GB 0322012.6 filed Sep. 19, 2003, the contents of which are incorporated herein by reference.

The present invention relates to novel silicon-containing amide derivatives, which have microbiocidal activity, in particular fungicidal activity. The invention also relates to novel intermediates used in the preparation of these compounds, to agrochemical compositions which comprise at least one of the novel compounds as active ingredient and to the use of the active ingredients or compositions in agriculture or horticulture for controlling or preventing infestation of plants by phytopathogenic microorganisms, preferably fungi.

Certain phenylamides and thiopheneamides, substituted by a silicon containing substituent as specified below, are disclosed in WO98/52944.

The present invention provides a compound of formula (I):

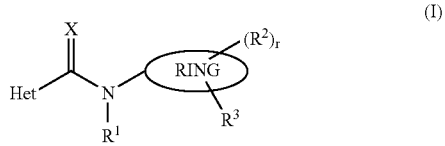

where X is O or S; RING is phenyl or thienyl; Het is a 5- or 6-membered heterocyclic ring containing one to three heteroatoms, each independently selected from oxygen, nitrogen and sulphur, the ring being substituted by one to four groups $R^4$; $R^1$ is hydrogen, optionally substituted $(C_{1-4})$alkyl, formyl, optionally substituted $(C_{1-4})$alkylC(=O), optionally substituted $(C_{1-4})$alkylC(=O)O, optionally substituted $(C_{1-4})$alkoxy$(C_{1-4})$alkyl, optionally substituted allyl, optionally substituted propargyl or optionally substituted allenyl; each $R^2$ is, independently, halogen, optionally substituted $(C_{1-4})$alkyl, optionally substituted $(C_{1-4})$alkoxy or optionally substituted $(C_{1-4})$alkoxy$(C_{1-4})$alkyl; $R^3$ is $(CR^aR^b)_m$—Cy—$(CR^cR^d)_n$—Y; each $R^4$ is, independently, selected from halogen, $C_{1-3}$ alkyl, $C_{1-3}$ haloalkyl, $C_{1-3}$ alkoxy$(C_{1-3})$alkyl and cyano; $R^a$, $R^b$, $R^c$ and $R^d$ are each, independently, hydrogen or optionally substituted $(C_{1-4})$alkyl; Cy is an optionally substituted carbocyclic or heterocyclic 3-7 membered ring which may be saturated, unsaturated or aromatic and which optionally contains a silicon atom as a ring member; $(CR^aR^b)_m$ and $(CR^cR^d)_n$ may be bound either to the same carbon or silicon atom of Cy or to different atoms separated by 1, 2 or 3 ring members; Y is $Si(O_pZ^1)(O_qZ^2)(O_sZ)$ and provided that Cy contains a silicon atom as a ring member then Y may also be hydrogen; Z is $C_{1-4}$ alkyl or $C_{2-4}$ alkenyl (each of which is optionally interrupted by one heteroatom selected from O, S and N and is optionally substituted by one to three independently selected halogen atoms); $Z^1$ and $Z^2$ are, independently, methyl or ethyl; m and n are each, independently, 0, 1, 2 or 3; p, q and s are each, independently, 0 or 1; and r is 0, 1 or 2; or an N-oxide thereof; provided that Y is not tri($C_{1-4}$)alkylsilyl when m and n are both 0 and RING and Cy are both phenyl.

Halogen is fluorine, chlorine, bromine or iodine, preferably fluorine, chlorine or bromine.

Each alkyl moiety is branched or unbranched and is, for example, methyl, ethyl, n-propyl, n-butyl, iso-propyl, sec-butyl, iso-butyl or tert-butyl.

Each alkenyl moiety is branched or unbranched.

Each alkenyl moiety, where appropriate, may be of either the (E)- or (Z)-configuration.

When present, each optional substituent on alkyl moieties, allyl, propargyl and allenyl is, independently, selected from halogen, hydroxy, cyano, carboxyl, methoxycarbonyl, ethoxycarbonyl, methoxy, ethoxy, methylsulfonyl, ethylsulfonyl, difluoromethoxy, trifluoromethoxy and trifluoromethylthio; in an alternative aspect of the invention, when present, each optional substituent on alkyl moieties, allyl, propargyl and allenyl is, independently, selected from halogen, hydroxy, cyano, carboxyl, methoxycarbonyl, ethoxycarbonyl, methoxy, ethoxy, methylsulfonyl, ethylsulfonyl, difluoromethoxy, trifluoromethoxy and trifluorothiomethoxy.

When present each optional substituent on Cy is, independently, selected from halogen, $(C_{1-4})$alkyl, $(C_{2-4})$alkenyl, $(C_{1-4})$haloalkyl, $(C_{1-4})$alkoxy and halo$(C_{1-4})$alkoxy.

Preferably X is oxygen.

Preferably, when "RING" is thienyl, the $N(R^1)CX$Het group is attached at position 3.

It is preferred that Het is pyrazolyl, pyrrolyl, thiophenyl, furyl, thiazolyl, isothiazolyl, oxazolyl, isoxazolyl, triazolyl, pyridinyl, pyrazinyl, pyrimidinyl, pyridazinyl, 5.6-dihydropyranyl or 5.6-dihydro-1.4-oxathiinyl (more preferably pyrazolyl, pyrrolyl, thiophenyl, furyl, thiazolyl, oxazolyl, 1,2,3-triazolyl, pyridinyl, pyrimidinyl, pyridazinyl, 5.6-dihydropyranyl or 5.6-dihydro-1.4-oxathiinyl; most preferably pyrazolyl, pyrrolyl, thiazolyl, 1,2,3-triazolyl or pyridinyl) each being substituted by one to three groups $R^4$ and connected to the group $C(=X)—N(R^1)$ via a carbon atom.

Preferably $R^1$ is hydrogen, propargyl, allenyl, formyl, $CH_3C(=O)$, $C_2H_5C(=O)$ or $CH_3OCH_2C(=O)$; more preferably hydrogen, propargyl, allenyl, formyl, $CH_3C(=O)$ or $C_2H_5C(=O)$.

Most preferably $R^1$ is hydrogen.

Preferably each $R^2$ is, independently, selected from halogen, methyl, trifluoromethyl and trifluoromethoxy.

Preferably each $R^4$ is, independently, selected from halogen, methyl, $CF_3$, $CF_2H$, $CH_2F$, $CF_2Cl$ and $CH_2OCH_3$ Preferably the nitrogen atoms in the Het ring which are not bound to one of their neighbour atoms by a double bond are each, independently, either unsubstituted or are substituted by $R^4$ (more preferably they are each, independently, substituted by $R^4$); where each such $R^4$ is, independently, selected from $C_{1-3}$ alkyl, $C_{1-3}$ haloalkyl and methoxymethylene; more preferably from $C_{1-2}$ alkyl, $CF_3$, $CF_2Cl$, $CHF_2$, $CH_2F$ and methoxymethylene; even more preferably from methyl, $CHF_2$ and methoxymethylene; and is most preferably methyl.

Preferably the carbon atoms in the Het ring which are not bound to the atom substituted by the group $C(=X)—N(R^1)$ are each, independently, either unsubstituted or are substituted by $R^4$; where each such $R^4$ is, independently, selected from halogen, $C_{1-3}$ alkyl, $C_{1-3}$ haloalkyl and methoxymethylene; more preferably from chloro, methoxymethylene, $CH_3$, $CHF_2$ and $CF_3$; and even more preferably from $CH_3$, $CHF_2$ and $CF_3$.

There may be one or two carbon atoms in the Het ring bound to the atom substituted by the group $C(=X)—N(R^1)$, preferably one of these carbon atoms is substituted by $R^4$ which is, independently, selected, from halogen, $C_{1-3}$ alkyl and $C_{1-3}$ haloalkyl; more preferably from chloro, fluoro, bromo, $C_{1-2}$ alkyl, $CF_3$, $CF_2Cl$, $CHF_2$ and $CH_2F$; and even more preferably from chloro, fluoro, bromo, methyl, $CF_3$, $CHF_2$ and $CH_2F$. If present, the second carbon bound to the atom substituted by $CXNR^1$ is preferably unsubstituted or is substituted by $R^4$ which is, independently, selected from halogen; more preferably from fluorine and chlorine.

Preferably $(CR^aR^b)_m$—Cy—$(CR^cR^d)_n$—Y is attached to "RING" at a carbon next (ortho) to the carbon which carries the $N(R^1)C(=X)$Het group.

Preferably $R^a$, $R^b$, $R^c$ and $R^d$ are each, independently, hydrogen or methyl, most preferably hydrogen.

When Cy is a silacycle [that is, it contains a silicon atom as a ring member] it is preferred that m is 0 or 1 (more preferably 0), n is 1 or 2 (more preferably 1) and Y is hydrogen.

When Cy is other than a silacycle it is preferred that nm is preferably 0 or 1 (more preferably 0) and n is preferably 0, 1 or 2.

Preferably Cy is a carbocyclic saturated 3-7 membered ring optionally substituted with up to 4 substituents (preferably each of these substituents is, independently, selected from $C_{1-4}$ alkyl; more preferably each is methyl), a 5-7 membered carbocyclic ring containing one double bond optionally substituted with up to 4 substituents (preferably each of these o substituents is, independently, selected from $C_{1-4}$ alkyl; more preferably each is methyl), a 4-7 membered saturated or unsaturated silacycle optionally substituted with up to 4 substituents (preferably each of these substituents is, independently, selected from $C_{1-4}$ allyl, $C_{2-4}$ alkenyl and $C_{1-4}$ alkoxy; more preferably from methyl, ethyl, propyl, iso-propyl, allyl, vinyl, methoxy and ethoxy) or Cy is phenyl, thiophenyl, furyl or pyridinyl, each optionally substituted with up to 4 substituents (each of which is preferably halogen, methyl, methoxy or trifluoromethoxy).

More preferably Cy is selected from the following rings:

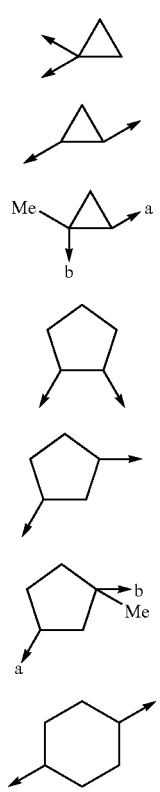

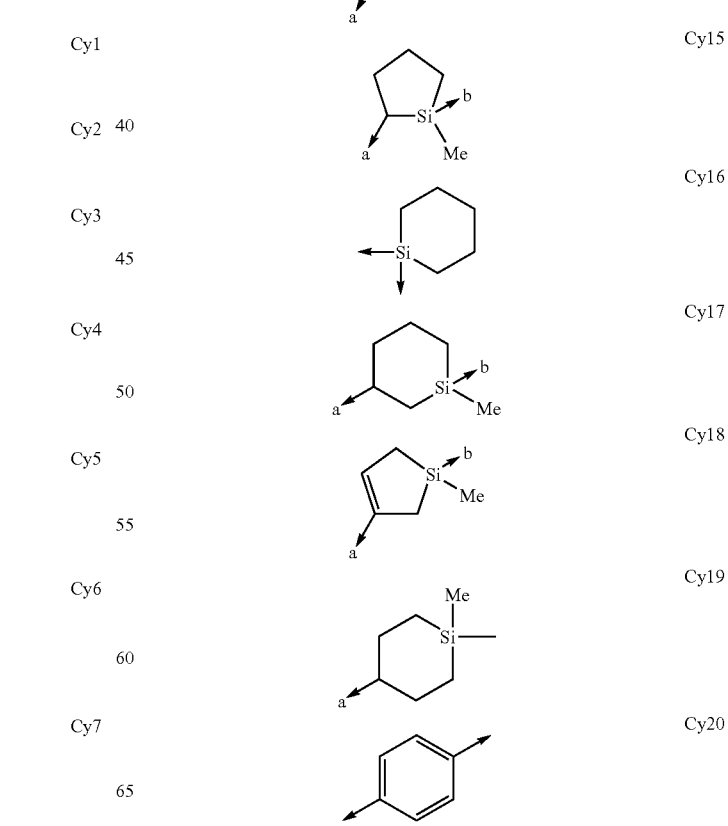

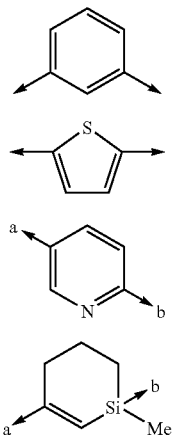

The symmetrical nature of Cy1, Cy2, Cy4, Cy5, Cy7, Cy8, Cy11, Cy12, Cy13, Cy16, Cy20, Cy21 and Cy22 means that it does not matter which arrow represents a bond to the moiety $(CR^aR^b)_m$ and which arrow represents a bond to the moiety $(CR^cR^d)_n$. However Cy3, Cy6, Cy9, Cy10, Cy14, Cy15, Cy17, Cy18, Cy19, Cy23 and Cy24 are not symmetric and therefore it does matter which arrow represents a bond to the moiety $(CR^aR^b)_m$ and which arrow represents a bond to the moiety $(CR^cR^d)_n$; for these values of Cy, it is preferred that the arrow labelled "a" represents a bond to the moiety $(CR^aR^b)_m$ [and therefore that the arrow labelled "b" represents a bond to the moiety$(CR^cR^d)_n$]. In this specification Cy3a is the group Cy3 in which the arrow "a" represents a bond to the moiety $(CR^aR^b)_m$; whilst Cy3b is the group Cy3 in which the arrow "b" represents a bond to the moiety $(CR^aR^b)_m$. The same applies *mutatis mutandis* to Cy6, Cy9, Cy10, Cy14, Cy15, Cy17, Cy18, Cy19, Cy23 and Cy24. In all instances, the "a" group is preferred to the corresponding "b" group.

Preferably $Z^1$ is methyl.
Preferably $Z^2$ is methyl.
Preferably Z is $C_{1-4}$ alkyl; more preferably methyl.
Preferably p is 0.
Preferably q is 0.
Preferably r is 0 or 1; more preferably r is 0.
Preferably s is 0.

When a compound of formula (I) is an N-oxide then it is preferred that Het is pyridinyl substituted by one to three groups $R^4$.

Throughout this description, Me is used to represent the methyl group. Likewise, Et represents the ethyl group.

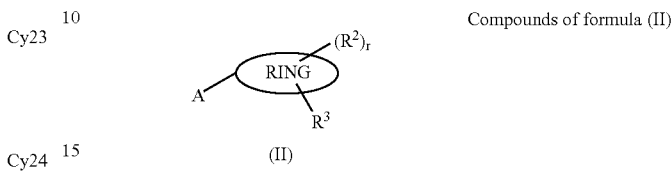

Compounds of formula (II)

where RING, r, $R^2$ and $R^3$ are as defined above and A is $NH_2$, NHCH(O), optionally substituted $(C_{1-4})$alkylC(=O)NH, optionally substituted $(C_{1-4})$alkylOC(=O)NH, halogen, $NO_2$, $OSO_2CF_3$ or $N=C(C_6H_5)_2$ are useful as intermediates in the preparation of compounds of formula (I).

Compounds of formula (D) where $R^3$ is bound to a carbon atom in a position ortho to A are novel and are preferred as intermediates for the preparation of compounds of formula (I).

Therefore, in another aspect the present invention provides a compound of formula (II) where RING, r, $R^2$ and $R^3$ are as defined above and A is $NH_2$, NHCH(O), optionally substituted $(C_{1-4})$alkylC(=O)NH, optionally substituted $(C_{1-4})$alkylOC(=O)NH, Br, I, $NO_2$, $OSO_2CF_3$ or $N=C(C_6H_5)_2$ and $R^3$ is bound to a carbon atom in a position ortho to A.

The compounds of formulae (I) and (II) may exist as different geometric or optical isomers or in different tautomeric forms. This invention covers all such isomers and tautomers and mixtures thereof in all proportions as well as isotopic forms such as deuterated compounds.

The compounds in Tables 1 to 29 below illustrate particularly preferred compounds of the invention, in which $R^5$, $R^6$ and $R^7$ are each, independently, examples of $R^4$ as defined above.

Table Aa represents Table 1a (when A is 1), represents Table 2a (when A is 2), represents Table 3a (when A is 3) and represents Table 4a (when A is 4).

TABLE Aa

| Compound No. | $R^1$ | m | n | Cy | Y | $R^5$ | $R^6$ | $R^7$ | X |
|---|---|---|---|---|---|---|---|---|---|
| A.1 | H | 0 | 0 | Cy1 | $Me_3Si$ | H | Me | $CF_3$ | O |
| A.2 | H | 0 | 0 | Cy1 | $Me_3Si$ | H | Me | $CF_2H$ | O |
| A.3 | H | 0 | 0 | Cy2 | $Me_3Si$ | H | Me | $CF_3$ | O |
| A.4 | H | 0 | 0 | Cy2 | $Me_3Si$ | H | Me | $CF_2H$ | O |
| A.5 | H | 0 | 0 | Cy2 | $Me_3Si$ | H | Me | $CF_2Cl$ | O |
| A.6 | H | 0 | 0 | Cy2 | $Me_3Si$ | H | Me | $CF_3$ | S |
| A.7 | propargyl | 0 | 0 | Cy2 | $Me_3Si$ | H | Me | $CF_3$ | O |
| A.8 | allenyl | 0 | 0 | Cy2 | $Me_3Si$ | H | Me | $CF_3$ | O |
| A.9 | $COCH_3$ | 0 | 0 | Cy2 | $Me_3Si$ | H | Me | $CF_3$ | O |
| A.10 | H | 0 | 0 | Cy2 | $Me_3Si$ | H | $CH_2OMe$ | $CF_3$ | O |
| A.11 | H | 0 | 0 | Cy2 | $Me_3Si$ | H | Me | $CF_2H$ | S |
| A.12 | propargyl | 0 | 0 | Cy2 | $Me_3Si$ | H | Me | $CF_2H$ | O |
| A.13 | allenyl | 0 | 0 | Cy2 | $Me_3Si$ | H | Me | $CF_2H$ | O |
| A.14 | $COCH_3$ | 0 | 0 | Cy2 | $Me_3Si$ | H | Me | $CF_2H$ | O |
| A.15 | H | 0 | 0 | Cy2 | $Me_3Si$ | H | $CH_2OMe$ | $CF_2H$ | O |
| A.16 | H | 0 | 0 | Cy2 | $Me_3Si$ | F | Me | Me | O |
| A.17 | H | 0 | 0 | Cy2 | $Me_3Si$ | F | Me | $CF_3$ | O |
| A.18 | H | 0 | 0 | Cy2 | $Me_3Si$ | H | Me | $CH_2F$ | O |
| A.19 | H | 0 | 0 | Cy2 | $Me_3Si$ | Cl | Me | Me | O |

TABLE Aa-continued

| Compound No. | R¹ | m | n | Cy | Y | R⁵ | R⁶ | R⁷ | X |
|---|---|---|---|---|---|---|---|---|---|
| A.20 | H | 0 | 0 | Cy2 | Me₂SiEt | H | Me | CF₃ | O |
| A.21 | H | 0 | 0 | Cy2 | Me₂SiEt | H | Me | CF₂H | O |
| A.22 | H | 0 | 0 | Cy2 | Me₂SiCHMe₂ | H | Me | CF₃ | O |
| A.23 | H | 0 | 0 | Cy2 | Me₂SiCHMe₂ | H | Me | CF₂H | O |
| A.24 | H | 1 | 0 | Cy2 | Me₃Si | H | Me | CF₃ | O |
| A.25 | H | 1 | 0 | Cy2 | Me₃Si | H | Me | CF₂H | O |
| A.26 | H | 0 | 1 | Cy2 | Me₃Si | H | Me | CF₃ | O |
| A.27 | H | 0 | 1 | Cy2 | Me₃Si | H | Me | CF₂H | O |
| A.28a | H | 0 | 0 | Cy3a | Me₃Si | H | Me | CF₃ | O |
| A.29a | H | 0 | 0 | Cy3a | Me₃Si | H | Me | CF₂H | O |
| A.30 | H | 0 | 0 | Cy4 | Me₃Si | H | Me | CF₃ | O |
| A.31 | H | 0 | 0 | Cy4 | Me₃Si | H | Me | CF₂H | O |
| A.32 | H | 0 | 0 | Cy5 | Me₃Si | H | Me | CF₃ | O |
| A.33 | H | 0 | 0 | Cy5 | Me₃Si | H | Me | CF₂H | O |
| A.34a | H | 0 | 0 | Cy6a | Me₃Si | H | Me | CF₃ | O |
| A.35a | H | 0 | 0 | Cy6a | Me₃Si | H | Me | CF₂H | O |
| A.36 | H | 0 | 0 | Cy7 | Me₃Si | H | Me | CF₃ | O |
| A.37 | H | 0 | 0 | Cy7 | Me₃Si | H | Me | CF₂H | O |
| A.38 | H | 0 | 0 | Cy8 | Me₃Si | H | Me | CF₃ | O |
| A.39 | H | 0 | 0 | Cy8 | Me₃Si | H | Me | CF₂H | O |
| A.40a | H | 0 | 0 | Cy9a | Me₃Si | H | Me | CF₃ | O |
| A.41a | H | 0 | 0 | Cy9a | Me₃Si | H | Me | CF₂H | O |
| A.42a | H | 0 | 0 | Cy10a | Me₃Si | H | Me | CF₃ | O |
| A.43a | H | 0 | 0 | Cy10a | Me₃Si | H | Me | CF₂H | O |
| A.44 | H | 0 | 1 | Cy11 | H | H | Me | CF₃ | O |
| A.45 | H | 0 | 1 | Cy11 | H | H | Me | CF₂H | O |
| A.46 | H | 0 | 1 | Cy12 | H | H | Me | CF₃ | O |
| A.47 | H | 0 | 1 | Cy12 | H | H | Me | CF₂H | O |
| A.48 | H | 0 | 1 | Cy13 | H | H | Me | CF₃ | O |
| A.49 | H | 0 | 1 | Cy13 | H | H | Me | CF₂H | O |
| A.50a | H | 0 | 1 | Cy14a | H | H | Me | CF₃ | O |
| A.51a | H | 0 | 1 | Cy14a | H | H | Me | CF₂H | O |
| A.52a | propargyl | 0 | 1 | Cy14a | H | H | Me | CF₃ | O |
| A.53a | allenyl | 0 | 1 | Cy14a | H | H | Me | CF₂H | O |
| A.54a | propargyl | 0 | 1 | Cy14a | H | H | Me | CF₂H | O |
| A.55a | allenyl | 0 | 1 | Cy14a | H | H | Me | CF₃ | O |
| A.56a | H | 0 | 1 | Cy15a | H | H | Me | CF₃ | O |
| A.57a | H | 0 | 1 | Cy15a | H | H | Me | CF₂H | O |
| A.58 | H | 0 | 1 | Cy16 | H | H | Me | CF₃ | O |
| A.59 | H | 0 | 1 | Cy16 | H | H | Me | CF₂H | O |
| A.60a | H | 0 | 1 | Cy17a | H | H | Me | CF₃ | O |
| A.61a | H | 0 | 1 | Cy17a | H | H | Me | CF₂H | O |
| A.62a | propargyl | 0 | 1 | Cy17a | H | H | Me | CF₃ | O |
| A.63a | allenyl | 0 | 1 | Cy17a | H | H | Me | CF₂H | O |
| A.64a | propargyl | 0 | 1 | Cy17a | H | H | Me | CF₂H | O |
| A.65a | allenyl | 0 | 1 | Cy17a | H | H | Me | CF₃ | O |
| A.66a | H | 0 | 1 | Cy17a | H | H | Me | CH₂F | O |
| A.67a | H | 0 | 1 | Cy17a | H | F | Me | Me | O |
| A.68a | H | 0 | 1 | Cy18a | H | H | Me | CF₂H | O |
| A.69a | H | 0 | 1 | Cy18a | H | H | Me | CF₃ | O |
| A.70a | H | 0 | 1 | Cy19a | H | H | Me | CF₃ | O |
| A.71a | H | 0 | 1 | Cy19a | H | H | Me | CF₂H | O |
| A.72a | propargyl | 0 | 1 | Cy19a | H | H | Me | CF₃ | O |
| A.73a | allenyl | 0 | 1 | Cy19a | H | H | Me | CF₂H | O |
| A.74a | propargyl | 0 | 1 | Cy19a | H | H | Me | CF₂H | O |
| A.75a | allenyl | 0 | 1 | Cy19a | H | H | Me | CF₃ | O |
| A.76a | H | 0 | 1 | Cy19a | H | H | Me | CH₂F | O |
| A.77a | H | 0 | 1 | Cy19a | H | F | Me | Me | O |
| A.78a | H | 0 | 2 | Cy17a | H | H | Me | CF₃ | O |
| A.79 | H | 0 | 0 | Cy2 | Me₃Si | H | CF₂H | CF₃ | O |
| A.80 | H | 0 | 0 | Cy20 | Me₂SiCMe₃ | H | Me | CF₃ | O |
| A.81 | H | 0 | 0 | Cy20 | Me₂SiCMe₃ | H | Me | CF₂H | O |
| A.82 | H | 0 | 1 | Cy20 | Me₃Si | H | Me | CF₃ | O |
| A.83 | H | 0 | 1 | Cy20 | Me₃Si | H | Me | CF₂H | O |
| A.84 | H | 0 | 2 | Cy20 | Me₃Si | H | Me | CF₃ | O |
| A.85 | H | 0 | 2 | Cy20 | Me₃Si | H | Me | CF₂H | O |
| A.86 | H | 0 | 0 | Cy21 | Me₃Si | H | Me | CF₃ | O |
| A.87 | H | 0 | 0 | Cy21 | Me₃Si | H | Me | CF₂H | O |
| A.88 | H | 0 | 0 | Cy22 | Me₃Si | H | Me | CF₃ | O |
| A.89 | H | 0 | 0 | Cy22 | Me₃Si | H | Me | CF₂H | O |
| A.90 | CHO | 0 | 0 | Cy22 | Me₃Si | H | Me | CF₃ | O |
| A.91 | CHO | 0 | 0 | Cy22 | Me₃Si | H | Me | CF₂H | O |
| A.92a | H | 0 | 0 | Cy23a | Me₃Si | H | Me | CF₃ | O |
| A.93a | H | 0 | 0 | Cy23a | Me₃Si | H | Me | CF₂H | O |
| A.94a | H | 0 | 1 | Cy24a | H | H | Me | CF₃ | O |
| A.95a | H | 0 | 1 | Cy24a | H | H | Me | CF₂H | O |

TABLE Aa-continued

| Compound No. | R¹ | m | n | Cy | Y | R⁵ | R⁶ | R⁷ | X |
|---|---|---|---|---|---|---|---|---|---|
| A.96a | H | 0 | 2 | Cy17a | H | H | Me | CF$_2$H | O |
| A.97a | H | 1 | 1 | Cy19a | H | H | Me | CF$_3$ | O |
| A.98a | H | 1 | 1 | Cy19a | H | H | Me | CF$_2$H | O |

Table Ab represents Table 1b (when A is 1), represents Table 2b (when A is 2), represents Table 3b (when A is 3) and represents Table 4b (when A is 4).

TABLE Ab

| Compound No. | R¹ | m | n | Cy | Y | R⁵ | R⁶ | R⁷ | X |
|---|---|---|---|---|---|---|---|---|---|
| A.28b | H | 0 | 0 | Cy3b | Me$_3$Si | H | Me | CF$_3$ | O |
| A.29b | H | 0 | 0 | Cy3b | Me$_3$Si | H | Me | CF$_2$H | O |
| A.34b | H | 0 | 0 | Cy6b | Me$_3$Si | H | Me | CF$_3$ | O |
| A.35b | H | 0 | 0 | Cy6b | Me$_3$Si | H | Me | CF$_2$H | O |
| A.40b | H | 0 | 0 | Cy9b | Me$_3$Si | H | Me | CF$_3$ | O |
| A.41b | H | 0 | 0 | Cy9b | Me$_3$Si | H | Me | CF$_2$H | O |
| A.42b | H | 0 | 0 | Cy10b | Me$_3$Si | H | Me | CF$_3$ | O |
| A.43b | H | 0 | 0 | Cy10b | Me$_3$Si | H | Me | CF$_2$H | O |
| A.50b | H | 0 | 1 | Cy14b | H | H | Me | CF$_3$ | O |
| A.51b | H | 0 | 1 | Cy14b | H | H | Me | CF$_2$H | O |
| A.52b | propargyl | 0 | 1 | Cy14b | H | H | Me | CF$_3$ | O |
| A.53b | allenyl | 0 | 1 | Cy14b | H | H | Me | CF$_2$H | O |
| A.54b | propargyl | 0 | 1 | Cy14b | H | H | Me | CF$_2$H | O |
| A.55b | allenyl | 0 | 1 | Cy14b | H | H | Me | CF$_3$ | O |
| A.56b | H | 0 | 1 | Cy15b | H | H | Me | CF$_3$ | O |
| A.57b | H | 0 | 1 | Cy15b | H | H | Me | CF$_2$H | O |
| A.60b | H | 0 | 1 | Cy17b | H | H | Me | CF$_3$ | O |
| A.61b | H | 0 | 1 | Cy17b | H | H | Me | CF$_2$H | O |
| A.62b | propargyl | 0 | 1 | Cy17b | H | H | Me | CF$_3$ | O |
| A.63b | allenyl | 0 | 1 | Cy17b | H | H | Me | CF$_2$H | O |
| A.64b | propargyl | 0 | 1 | Cy17b | H | H | Me | CF$_2$H | O |
| A.65b | allenyl | 0 | 1 | Cy17b | H | H | Me | CF$_3$ | O |
| A.66b | H | 0 | 1 | Cy17b | H | H | Me | CH$_2$F | O |
| A.67b | H | 0 | 1 | Cy17b | H | F | Me | Me | O |
| A.68b | H | 0 | 1 | Cy18b | H | H | Me | CF$_2$H | O |
| A.69b | H | 0 | 1 | Cy18b | H | H | Me | CF$_3$ | O |
| A.70b | H | 0 | 1 | Cy19b | H | H | Me | CF$_3$ | O |
| A.71b | H | 0 | 1 | Cy19b | H | H | Me | CF$_2$H | O |
| A.72b | propargyl | 0 | 1 | Cy19b | H | H | Me | CF$_3$ | O |
| A.73b | allenyl | 0 | 1 | Cy19b | H | H | Me | CF$_2$H | O |
| A.74b | propargyl | 0 | 1 | Cy19b | H | H | Me | CF$_2$H | O |
| A.75b | allenyl | 0 | 1 | Cy19b | H | H | Me | CF$_3$ | O |
| A.76b | H | 0 | 1 | Cy19b | H | H | Me | CH$_2$F | O |
| A.77b | H | 0 | 1 | Cy19b | H | F | Me | Me | O |
| A.78b | H | 0 | 2 | Cy17b | H | H | Me | CF$_3$ | O |
| A.92b | H | 0 | 0 | Cy23b | Me$_3$Si | H | Me | CF$_3$ | O |
| A.93b | H | 0 | 0 | Cy23b | Me$_3$Si | H | Me | CF$_2$H | O |
| A.94b | H | 0 | 1 | Cy24b | H | H | Me | CF$_3$ | O |
| A.95b | H | 0 | 1 | Cy24b | H | H | Me | CF$_2$H | O |

Table 1a provides 98 compounds of formula (Ia) where R¹, m, n, Cy, R⁵, R⁶, R⁷ Y and X are as defined in Table 1a.

Table 1b provides 39 compounds of formula (Ia) where R¹, m, n, Cy, R⁵, R⁶, R⁷ Y and 5 X are as defined in Table 1b.

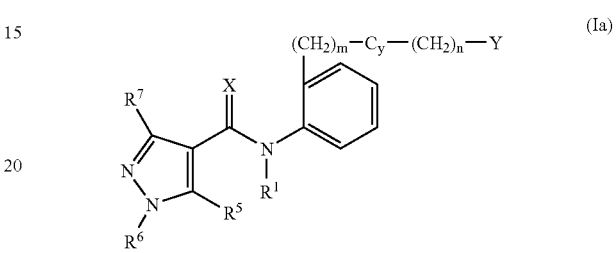

(Ia)

Table 2a provides 98 compounds of formula (Iaa) where R¹, m, n, Cy, R⁵, R⁶, R⁷ Y and X are as defined in Table 2a.

Table 2b provides 39 compounds of formula (Iaa) where R¹, m, n, Cy, R⁵, R⁶, R⁷ Y and X are as defined in Table 2b.

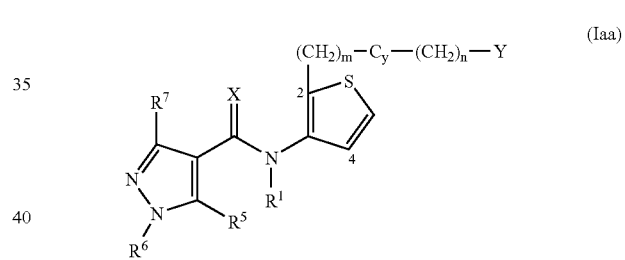

(Iaa)

Table 3a provides 98 compounds of formula (Ib) where R¹, m, n, Cy, R⁵, R⁶, R⁷ Y and X are as defined in Table 3a.

Table 3b provides 39 compounds of formula (Ib) where R¹, m, n, Cy, R⁵, R⁶, R⁷ Y and X are as defined in Table 3b.

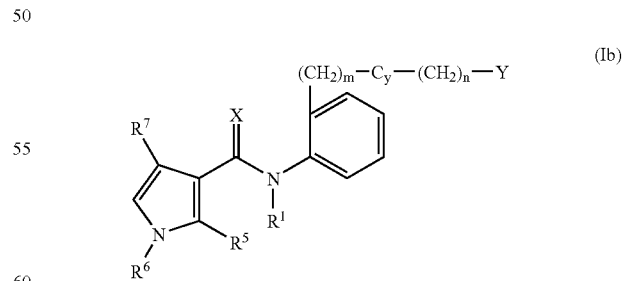

(Ib)

Table 4a provides 98 compounds of formula (Ibb) R¹, m, n, Cy, R⁵, R⁶, R⁷ Y and X are as defined in Table 4a.

Table 4b provides 39 compounds of formula (Ibb) R¹, m, n, Cy, R⁵, R⁶, R⁷ Y and X are as defined in Table 4b.

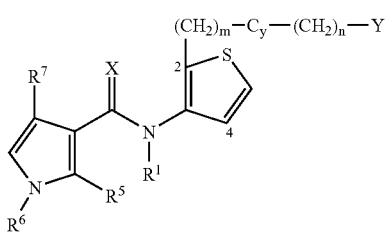

(Ibb)

Table Ba represents Table 5a (when B is 5), represents Table 6a (when B is 6), represents Table 7a (when B is 7), represents Table 8a (when B is 8), represents Table 9a (when B is 9) and represents Table 10a (when B is 10).

TABLE Ba

| Compound No. | $R^1$ | m | n | Cy | Y | $R^5$ | $R^6$ | X |
|---|---|---|---|---|---|---|---|---|
| B.1 | H | 0 | 0 | Cy1 | $Me_3Si$ | Me | $CF_3$ | O |
| B.2 | H | 0 | 0 | Cy1 | $Me_3Si$ | Me | $CF_2H$ | O |
| B.3 | H | 0 | 0 | Cy2 | $Me_3Si$ | Me | $CF_3$ | O |
| B.4 | H | 0 | 0 | Cy2 | $Me_3Si$ | Me | $CF_2H$ | O |
| B.5 | H | 0 | 0 | Cy2 | $Me_3Si$ | Me | $CF_2Cl$ | O |
| B.6 | H | 0 | 0 | Cy2 | $Me_3Si$ | Me | $CF_3$ | S |
| B.7 | propargyl | 0 | 0 | Cy2 | $Me_3Si$ | Me | $CF_3$ | O |
| B.8 | allenyl | 0 | 0 | Cy2 | $Me_3Si$ | Me | $CF_3$ | O |
| B.9 | $COCH_3$ | 0 | 0 | Cy2 | $Me_3Si$ | Me | $CF_3$ | O |
| B.10 | H | 0 | 0 | Cy2 | $Me_3Si$ | $CH_2OMe$ | $CF_3$ | O |
| B.11 | H | 0 | 0 | Cy2 | $Me_3Si$ | Me | $CF_2H$ | S |
| B.12 | propargyl | 0 | 0 | Cy2 | $Me_3Si$ | Me | $CF_2H$ | O |
| B.13 | allenyl | 0 | 0 | Cy2 | $Me_3Si$ | Me | $CF_2H$ | O |
| B.14 | $COCH_3$ | 0 | 0 | Cy2 | $Me_3Si$ | Me | $CF_2H$ | O |
| B.15 | H | 0 | 0 | Cy2 | $Me_3Si$ | $CH_2OMe$ | $CF_2H$ | O |
| B.16 | H | 0 | 0 | Cy2 | $Me_3Si$ | Me | Me | O |
| B.17 | H | 0 | 0 | Cy2 | $Me_3Si$ | $CF_3$ | Me | O |
| B.18 | H | 0 | 0 | Cy2 | $Me_3Si$ | Me | $CH_2F$ | O |
| B.19 | H | 0 | 0 | Cy2 | $Me_3Si$ | Me | $CH_2F$ | O |
| B.20 | H | 0 | 0 | Cy2 | $Me_2SiEt$ | Me | $CF_3$ | O |
| B.21 | H | 0 | 0 | Cy2 | $Me_2SiEt$ | Me | $CF_2H$ | O |
| B.22 | H | 0 | 0 | Cy2 | $Me_2SiCHMe_2$ | Me | $CF_3$ | O |
| B.23 | H | 0 | 0 | Cy2 | $Me_2SiCHMe_2$ | Me | $CF_2H$ | O |
| B.24 | H | 1 | 0 | Cy2 | $Me_3Si$ | Me | $CF_3$ | O |
| B.25 | H | 1 | 0 | Cy2 | $Me_3Si$ | Me | $CF_2H$ | O |
| B.26 | H | 0 | 1 | Cy2 | $Me_3Si$ | Me | $CF_3$ | O |
| B.27 | H | 0 | 1 | Cy2 | $Me_3Si$ | Me | $CF_2H$ | O |
| B.28a | H | 0 | 0 | Cy3a | $Me_3Si$ | Me | $CF_3$ | O |
| B.29a | H | 0 | 0 | Cy3a | $Me_3Si$ | Me | $CF_2H$ | O |
| B.30 | H | 0 | 0 | Cy4 | $Me_3Si$ | Me | $CF_3$ | O |
| B.31 | H | 0 | 0 | Cy4 | $Me_3Si$ | Me | $CF_2H$ | O |
| B.32 | H | 0 | 0 | Cy5 | $Me_3Si$ | Me | $CF_3$ | O |
| B.33 | H | 0 | 0 | Cy5 | $Me_3Si$ | Me | $CF_2H$ | O |
| B.34a | H | 0 | 0 | Cy6a | $Me_3Si$ | Me | $CF_3$ | O |
| B.35a | H | 0 | 0 | Cy6a | $Me_3Si$ | Me | $CF_2H$ | O |
| B.36 | H | 0 | 0 | Cy7 | $Me_3Si$ | Me | $CF_3$ | O |
| B.37 | H | 0 | 0 | Cy7 | $Me_3Si$ | Me | $CF_2H$ | O |
| B.38 | H | 0 | 0 | Cy8 | $Me_3Si$ | Me | $CF_3$ | O |
| B.39 | H | 0 | 0 | Cy8 | $Me_3Si$ | Me | $CF_2H$ | O |
| B.40a | H | 0 | 0 | Cy9a | $Me_3Si$ | Me | $CF_3$ | O |
| B.41a | H | 0 | 0 | Cy9a | $Me_3Si$ | Me | $CF_2H$ | O |
| B.42a | H | 0 | 0 | Cy10a | $Me_3Si$ | Me | $CF_3$ | O |
| B.43a | H | 0 | 0 | Cy10a | $Me_3Si$ | Me | $CF_2H$ | O |
| B.44 | H | 0 | 1 | Cy11 | H | Me | $CF_3$ | O |
| B.45 | H | 0 | 1 | Cy11 | H | Me | $CF_2H$ | O |
| B.46 | H | 0 | 1 | Cy12 | H | Me | $CF_3$ | O |
| B.47 | H | 0 | 1 | Cy12 | H | Me | $CF_2H$ | O |
| B.48 | H | 0 | 1 | Cy13 | H | Me | $CF_3$ | O |
| B.49 | H | 0 | 1 | Cy13 | H | Me | $CF_2H$ | O |
| B.50a | H | 0 | 1 | Cy14a | H | Me | $CF_3$ | O |
| B.51a | H | 0 | 1 | Cy14a | H | Me | $CF_2H$ | O |
| B.52a | propargyl | 0 | 1 | Cy14a | H | Me | $CF_3$ | O |
| B.53a | allenyl | 0 | 1 | Cy14a | H | Me | $CF_2H$ | O |
| B.54a | propargyl | 0 | 1 | Cy14a | H | Me | $CF_2H$ | O |
| B.55a | allenyl | 0 | 1 | Cy14a | H | Me | $CF_3$ | O |
| B.56a | H | 0 | 1 | Cy15a | H | Me | $CF_3$ | O |
| B.57a | H | 0 | 1 | Cy15a | H | Me | $CF_2H$ | O |
| B.58 | H | 0 | 1 | Cy16 | H | Me | $CF_3$ | O |
| B.59 | H | 0 | 1 | Cy16 | H | Me | $CF_2H$ | O |

TABLE Ba-continued

| Compound No. | R¹ | m | n | Cy | Y | R⁵ | R⁶ | X |
|---|---|---|---|---|---|---|---|---|
| B.60a | H | 0 | 1 | Cy17a | H | Me | CF₃ | O |
| B.61a | H | 0 | 1 | Cy17a | H | Me | CF₂H | O |
| B.62a | propargyl | 0 | 1 | Cy17a | H | Me | CF₃ | O |
| B.63a | allenyl | 0 | 1 | Cy17a | H | Me | CF₂H | O |
| B.64a | propargyl | 0 | 1 | Cy17a | H | Me | CF₂H | O |
| B.65a | allenyl | 0 | 1 | Cy17a | H | Me | CF₃ | O |
| B.66a | H | 0 | 1 | Cy17a | H | Me | CH₂F | O |
| B.67a | H | 0 | 1 | Cy17a | H | Me | Me | O |
| B.68a | H | 0 | 1 | Cy18a | H | Me | CF₂H | O |
| B.69a | H | 0 | 1 | Cy18a | H | Me | CF₃ | O |
| B.70a | H | 0 | 1 | Cy19a | H | Me | CF₃ | O |
| B.71a | H | 0 | 1 | Cy19a | H | Me | CF₂H | O |
| B.72a | propargyl | 0 | 1 | Cy19a | H | Me | CF₃ | O |
| B.73a | allenyl | 0 | 1 | Cy19a | H | Me | CF₂H | O |
| B.74a | propargyl | 0 | 1 | Cy19a | H | Me | CF₂H | O |
| B.75a | allenyl | 0 | 1 | Cy19a | H | Me | CF₃ | O |
| B.76a | H | 0 | 1 | Cy19a | H | Me | CH₂F | O |
| B.77a | H | 0 | 1 | Cy19a | H | Me | Me | O |
| B.78a | H | 0 | 2 | Cy17a | H | Me | CF₃ | O |
| B.79a | H | 0 | 2 | Cy17a | H | Me | CF₂H | O |
| B.80 | H | 0 | 0 | Cy20 | Me₂SiCMe₃ | Me | CF₃ | O |
| B.81 | H | 0 | 0 | Cy20 | Me₂SiCMe₃ | Me | CF₂H | O |
| B.82 | H | 0 | 1 | Cy20 | Me₃Si | Me | CF₃ | O |
| B.83 | H | 0 | 1 | Cy20 | Me₃Si | Me | CF₂H | O |
| B.84 | H | 0 | 2 | Cy20 | Me₃Si | Me | CF₃ | O |
| B.85 | H | 0 | 2 | Cy20 | Me₃Si | Me | CF₂H | O |
| B.86 | H | 0 | 0 | Cy21 | Me₃Si | Me | CF₃ | O |
| B.87 | H | 0 | 0 | Cy21 | Me₃Si | Me | CF₂H | O |
| B.88 | H | 0 | 0 | Cy22 | Me₃Si | Me | CF₃ | O |
| B.89 | H | 0 | 0 | Cy22 | Me₃Si | Me | CF₂H | O |
| B.90 | CHO | 0 | 0 | Cy22 | Me₃Si | Me | CF₃ | O |
| B.91 | CHO | 0 | 0 | Cy22 | Me₃Si | Me | CF₂H | O |
| B.92a | H | 0 | 0 | Cy23a | Me₃Si | Me | CF₃ | O |
| B.93a | H | 0 | 0 | Cy23a | Me₃Si | Me | CF₂H | O |
| B.94a | H | 0 | 1 | Cy24a | H | Me | CF₃ | O |
| B.95a | H | 0 | 1 | Cy24a | H | Me | CF₂H | O |
| B.96a | H | 0 | 2 | Cy17a | H | Me | CF₂H | O |
| B.97a | H | 1 | 1 | Cy19a | H | Me | CF₃ | O |
| B.98a | H | 1 | 1 | Cy19a | H | Me | CF₂H | O |

Table Bb represents Table 5b (when B is 5), represents Table 6b (when B is 6), represents Table 7b (when B is 7), represents Table-8b (when B is 8), represents Table 9b (when B is 9) and represents Table 10b (when B is 10).

TABLE Bb

| Compound No. | R¹ | m | n | Cy | Y | R⁵ | R⁶ | X |
|---|---|---|---|---|---|---|---|---|
| B.28b | H | 0 | 0 | Cy3b | Me₃Si | Me | CF₃ | O |
| B.29b | H | 0 | 0 | Cy3b | Me₃Si | Me | CF₂H | O |
| B.34b | H | 0 | 0 | Cy6b | Me₃Si | Me | CF₃ | O |
| B.35b | H | 0 | 0 | Cy6b | Me₃Si | Me | CF₂H | O |
| B.40b | H | 0 | 0 | Cy9b | Me₃Si | Me | CF₃ | O |
| B.41b | H | 0 | 0 | Cy9b | Me₃Si | Me | CF₂H | O |
| B.42b | H | 0 | 0 | Cy10b | Me₃Si | Me | CF₃ | O |
| B.43b | H | 0 | 0 | Cy10b | Me₃Si | Me | CF₂H | O |
| B.50b | H | 0 | 1 | Cy14b | H | Me | CF₃ | O |
| B.51b | H | 0 | 1 | Cy14b | H | Me | CF₂H | O |
| B.52b | propargyl | 0 | 1 | Cy14b | H | Me | CF₃ | O |
| B.53b | allenyl | 0 | 1 | Cy14b | H | Me | CF₂H | O |
| B.54b | propargyl | 0 | 1 | Cy14b | H | Me | CF₂H | O |
| B.55b | allenyl | 0 | 1 | Cy14b | H | Me | CF₃ | O |
| B.56b | H | 0 | 1 | Cy15b | H | Me | CF₃ | O |
| B.57b | H | 0 | 1 | Cy15b | H | Me | CF₂H | O |
| B.60b | H | 0 | 1 | Cy17b | H | Me | CF₃ | O |
| B.61b | H | 0 | 1 | Cy17b | H | Me | CF₂H | O |
| B.62b | propargyl | 0 | 1 | Cy17b | H | Me | CF₃ | O |
| B.63b | allenyl | 0 | 1 | Cy17b | H | Me | CF₂H | O |
| B.64b | propargyl | 0 | 1 | Cy17b | H | Me | CF₂H | O |
| B.65b | allenyl | 0 | 1 | Cy17b | H | Me | CF₃ | O |
| B.66b | H | 0 | 1 | Cy17b | H | Me | CH₂F | O |
| B.67b | H | 0 | 1 | Cy17b | H | Me | Me | O |
| B.68b | H | 0 | 1 | Cy18b | H | Me | CF₂H | O |
| B.69b | H | 0 | 1 | Cy18b | H | Me | CF₃ | O |
| B.70b | H | 0 | 1 | Cy19b | H | Me | CF₃ | O |
| B.71b | H | 0 | 1 | Cy19b | H | Me | CF₂H | O |
| B.72b | propargyl | 0 | 1 | Cy19b | H | Me | CF₃ | O |
| B.73b | allenyl | 0 | 1 | Cy19b | H | Me | CF₂H | O |
| B.74b | propargyl | 0 | 1 | Cy19b | H | Me | CF₂H | O |
| B.75b | allenyl | 0 | 1 | Cy19b | H | Me | CF₃ | O |
| B.76b | H | 0 | 1 | Cy19b | H | Me | CH₂F | O |
| B.77b | H | 0 | 1 | Cy19b | H | Me | Me | O |
| B.78b | H | 0 | 2 | Cy17b | H | Me | CF₃ | O |
| B.79b | H | 0 | 2 | Cy17b | H | Me | CF₂H | O |
| B.92b | H | 0 | 0 | Cy23b | Me₃Si | Me | CF₃ | O |
| B.93b | H | 0 | 0 | Cy23b | Me₃Si | Me | CF₂H | O |
| B.94b | H | 0 | 1 | Cy24b | H | Me | CF₃ | O |
| B.95b | H | 0 | 1 | Cy24b | H | Me | CF₂H | O |

Table 5a provides 98 compounds of formula (Ic) where $R^1$, m, n, Cy, $R^5$, $R^6$, Y and X are as defined in Table 5a.

Table 5b provides 40 compounds of formula (Ic) where $R^1$, m, n, Cy, $R^5$, $R^6$, Y and X are as defined in Table 5b.

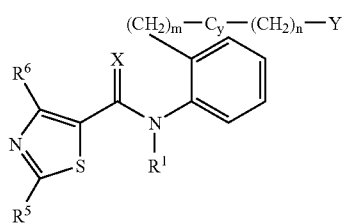

(Ic)

Table 6a provides 98 compounds of formula (Icc) where $R^1$, m, n, Cy, $R^5$, $R^6$, Y and X are as defined in Table 6a.
Table 6b provides 40 compounds of formula (Icc) where $R^1$, m, n, Cy, $R^5$, $R^6$, Y and X are as defined in Table 6b.

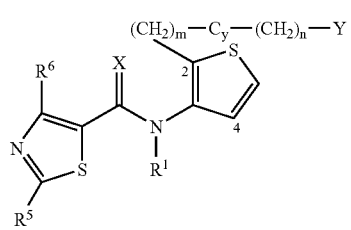

(Icc)

Table 7a provides 98 compounds of formula (Id) where $R^1$, m, n, Cy, $R^5$, $R^6$, Y and X are as defined in Table 7a.
Table 7b provides 40 compounds of formula (Id) where $R^1$, m, n, Cy, $R^5$, $R^6$, Y and X are as defined in Table 7b.

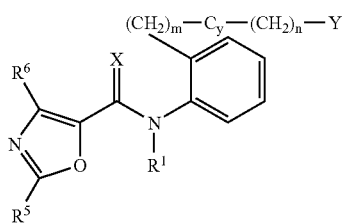

(Id)

Table 8a provides 98 compounds of formula (Idd) where $R^1$, m, n, Cy, $R^5$, $R^6$, Y and X are as defined in Table 8a.
Table 8b provides 40 compounds of formula (Idd) where $R^1$, m, n, Cy, $R^5$, $R^6$, Y and X are as defined in Table 8b.

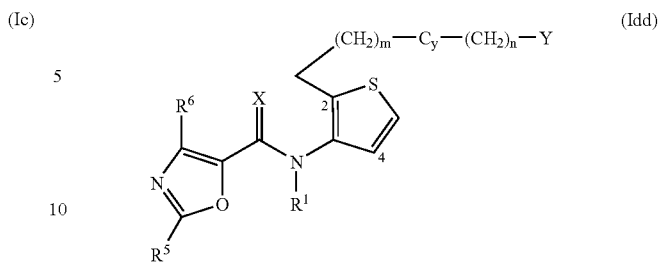

(Idd)

Table 9a provides 98 compounds of formula (Ie) where $R^1$, m, n, Cy, $R^5$, $R^6$, Y and X are as defined in Table 9a.
Table 9b provides 40 compounds of formula (Ie) where $R^1$, m, n, Cy, $R^5$, $R^6$, Y and X are as defined in Table 9b.

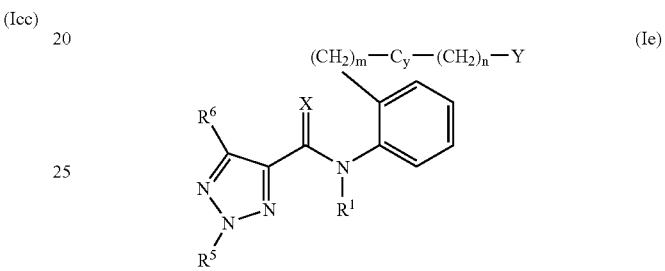

(Ie)

Table 10a provides 98 compounds of formula (Iee) where $R^1$, m, n, Cy, $R^5$, $R^6$, Y and X are as defined in Table 10a.
Table 10b provides 40 compounds of formula (Iee) where $R^1$, m, n, Cy, $R^5$, $R^6$, Y and X are as defined in Table 10b.

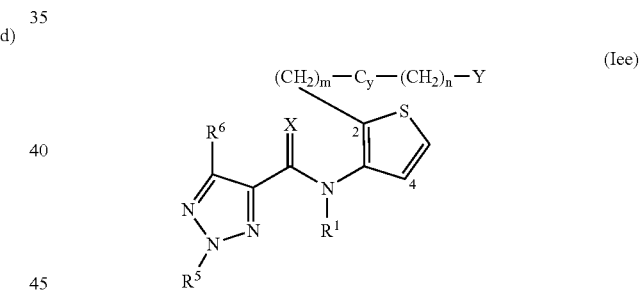

(Iee)

Table Ca represents Table 11a (when C is 11), represents Table 12a (when C is 12), represents Table 13a (when C is 13) and represents Table 14a (when C is 14).

TABLE Ca

| Compound No. | $R^1$ | m | n | Cy | Y | $R^5$ | $R^6$ | $R^7$ | X |
|---|---|---|---|---|---|---|---|---|---|
| C.1 | H | 0 | 0 | Cy1 | Me$_3$Si | H | Me | CF$_3$ | O |
| C.2 | H | 0 | 0 | Cy1 | Me$_3$Si | H | Me | CF$_2$H | O |
| C.3 | H | 0 | 0 | Cy2 | Me$_3$Si | H | Me | CF$_3$ | O |
| C.4 | H | 0 | 0 | Cy2 | Me$_3$Si | H | Me | CF$_2$H | O |
| C.5 | H | 0 | 0 | Cy2 | Me$_3$Si | H | Me | CF$_2$Cl | O |
| C.6 | H | 0 | 0 | Cy2 | Me$_3$Si | H | Me | CF$_3$ | S |
| C.7 | H | 0 | 0 | Cy2 | Me$_3$Si | Me | Me | CF$_3$ | O |
| C.8 | H | 0 | 0 | Cy2 | Me$_3$Si | H | H | CF$_3$ | O |
| C.9 | H | 0 | 0 | Cy2 | Me$_3$Si | Me | H | CF$_3$ | O |
| C.10 | H | 0 | 0 | Cy2 | Me$_3$Si | Me | Me | Me | O |
| C.11 | H | 0 | 0 | Cy2 | Me$_3$Si | Me | Me | H | O |
| C.12 | propargyl | 0 | 0 | Cy2 | Me$_3$Si | H | Me | CF$_3$ | O |

TABLE Ca-continued

| Compound No. | R¹ | m | n | Cy | Y | R⁵ | R⁶ | R⁷ | X |
|---|---|---|---|---|---|---|---|---|---|
| C.13 | allenyl | 0 | 0 | Cy2 | Me₃Si | H | Me | CF₃ | O |
| C.14 | COCH₃ | 0 | 0 | Cy2 | Me₃Si | H | Me | CF₃ | O |
| C.15 | H | 0 | 0 | Cy2 | Me₃Si | H | Me | CH₂F | O |
| C.16 | H | 1 | 0 | Cy2 | Me₃Si | H | Me | CF₃ | O |
| C.17 | H | 1 | 0 | Cy2 | Me₃Si | H | Me | CF₂H | O |
| C.18 | H | 0 | 1 | Cy2 | Me₃Si | H | Me | CF₃ | O |
| C.19 | H | 0 | 1 | Cy2 | Me₃Si | H | Me | CF₂H | O |
| C.20a | H | 0 | 0 | Cy3a | Me₃Si | H | Me | CF₃ | O |
| C.21a | H | 0 | 0 | Cy3a | Me₃Si | H | Me | CF₂H | O |
| C.22 | H | 0 | 0 | Cy4 | Me₃Si | H | Me | CF₃ | O |
| C.23 | H | 0 | 0 | Cy4 | Me₃Si | H | Me | CF₂H | O |
| C.24 | H | 0 | 0 | Cy5 | Me₃Si | H | Me | CF₃ | O |
| C.25 | H | 0 | 0 | Cy5 | Me₃Si | H | Me | CF₂H | O |
| C.26a | H | 0 | 0 | Cy6a | Me₃Si | H | Me | CF₃ | O |
| C.27a | H | 0 | 0 | Cy6a | Me₃Si | H | Me | CF₂H | O |
| C.28 | H | 0 | 0 | Cy7 | Me₃Si | H | Me | CF₃ | O |
| C.29 | H | 0 | 0 | Cy7 | Me₃Si | H | Me | CF₂H | O |
| C.30 | H | 0 | 0 | Cy8 | Me₃Si | H | Me | CF₃ | O |
| C.31 | H | 0 | 0 | Cy8 | Me₃Si | H | Me | CF₂H | O |
| C.32a | H | 0 | 0 | Cy9a | Me₃Si | H | Me | CF₃ | O |
| C.33a | H | 0 | 0 | Cy9a | Me₃Si | H | Me | CF₂H | O |
| C.34a | H | 0 | 0 | Cy10a | Me₃Si | H | Me | CF₃ | O |
| C.35a | H | 0 | 0 | Cy10a | Me₃Si | H | Me | CF₂H | O |
| C.36 | H | 0 | 1 | Cy11 | H | H | Me | CF₃ | O |
| C.37 | H | 0 | 1 | Cy11 | H | H | Me | CF₂H | O |
| C.38 | H | 0 | 1 | Cy12 | H | H | Me | CF₃ | O |
| C.39 | H | 0 | 1 | Cy12 | H | H | Me | CF₂H | O |
| C.40 | H | 0 | 1 | Cy13 | H | H | Me | CF₃ | O |
| C.41 | H | 0 | 1 | Cy13 | H | H | Me | CF₂H | O |
| C.42a | H | 0 | 1 | Cy14a | H | H | Me | CF₃ | O |
| C.43a | H | 0 | 1 | Cy14a | H | H | Me | CF₂H | O |
| C.44a | H | 0 | 1 | Cy14a | H | Me | Me | CF₃ | O |
| C.45a | H | 0 | 1 | Cy14a | H | H | H | CF₃ | O |
| C.46a | H | 0 | 1 | Cy14a | H | Me | H | CF₃ | O |
| C.47a | H | 0 | 1 | Cy14a | H | Me | Me | Me | O |
| C.48a | H | 0 | 1 | Cy14a | H | Me | Me | H | O |
| C.49a | H | 0 | 1 | Cy15a | H | Me | Me | CF₃ | O |
| C.50a | H | 0 | 1 | Cy15a | H | H | Me | CF₂H | O |
| C.51 | H | 0 | 1 | Cy16 | H | H | Me | CF₃ | O |
| C.52 | H | 0 | 1 | Cy16 | H | H | Me | CF₂H | O |
| C.53a | H | 0 | 1 | Cy17a | H | H | Me | CF₃ | O |
| C.54a | H | 0 | 1 | Cy17a | H | H | Me | CF₂H | O |
| C.55a | H | 0 | 1 | Cy17a | H | Me | Me | CF₃ | O |
| C.56a | H | 0 | 1 | Cy17a | H | H | H | CF₃ | O |
| C.57a | H | 0 | 1 | Cy17a | H | Me | H | CF₃ | O |
| C.58a | H | 0 | 1 | Cy17a | H | Me | Me | Me | O |
| C.59a | H | 0 | 1 | Cy17a | H | Me | Me | H | O |
| C.60a | H | 0 | 1 | Cy18a | H | H | Me | CF₂H | O |
| C.61a | H | 0 | 1 | Cy18a | H | H | Me | CF₃ | O |
| C.62a | H | 0 | 1 | Cy19a | H | H | Me | CF₃ | O |
| C.63a | H | 0 | 1 | Cy19a | H | H | Me | CF₂H | O |
| C.64a | H | 0 | 1 | Cy19a | H | Me | Me | CF₃ | O |
| C.65a | H | 0 | 1 | Cy19a | H | H | H | CF₃ | O |
| C.66a | H | 0 | 1 | Cy19a | H | Me | H | CF₃ | O |
| C.67a | H | 0 | 1 | Cy19a | H | Me | Me | Me | O |
| C.68a | H | 0 | 1 | Cy19a | H | Me | Me | H | O |
| C.69a | H | 0 | 2 | Cy17a | H | H | Me | CF₃ | O |
| C.70a | H | 0 | 2 | Cy17a | H | H | Me | CF₂H | O |
| C.71 | H | 0 | 0 | Cy20 | Me₂SiCMe₃ | H | Me | CF₃ | O |
| C.72 | H | 0 | 0 | Cy20 | Me₂SiCMe₃ | H | Me | CF₂H | O |
| C.73 | H | 0 | 1 | Cy20 | Me₃Si | H | Me | CF₃ | O |
| C.74 | H | 0 | 2 | Cy20 | Me₃Si | H | Me | CF₃ | O |
| C.75 | H | 0 | 0 | Cy21 | Me₃Si | H | Me | CF₃ | O |
| C.76 | H | 0 | 0 | Cy22 | Me₃Si | H | Me | CF₃ | O |
| C.77 | CHO | 0 | 0 | Cy22 | Me₃Si | H | Me | CF₃ | O |
| C.78a | H | 0 | 0 | Cy23a | Me₃Si | H | Me | CF₃ | O |
| C.79a | H | 0 | 1 | Cy24a | H | H | Me | CF₂H | O |
| C.80a | H | 0 | 1 | Cy24a | H | Me | Me | CF₃ | O |

Table Cb represents Table 11b (when C is 11), represents Table 12b (when C is 12), represents Table 13b (when C is 13) and represents Table 14b (when C is 14).

TABLE Cb

| Compound No. | $R^1$ | m | n | Cy | Y | $R^5$ | $R^6$ | $R^7$ | X |
|---|---|---|---|---|---|---|---|---|---|
| C.20b | H | 0 | 0 | Cy3b | Me$_3$Si | H | Me | CF$_3$ | O |
| C.21b | H | 0 | 0 | Cy3b | Me$_3$Si | H | Me | CF$_2$H | O |
| C.26b | H | 0 | 0 | Cy6b | Me$_3$Si | H | Me | CF$_3$ | O |
| C.27b | H | 0 | 0 | Cy6b | Me$_3$Si | H | Me | CF$_2$H | O |
| C.32b | H | 0 | 0 | Cy9b | Me$_3$Si | H | Me | CF$_3$ | O |
| C.33b | H | 0 | 0 | Cy9b | Me$_3$Si | H | Me | CF$_2$H | O |
| C.34b | H | 0 | 0 | Cy10b | Me$_3$Si | H | Me | CF$_3$ | O |
| C.35b | H | 0 | 0 | Cy10b | Me$_3$Si | H | Me | CF$_2$H | O |
| C.42b | H | 0 | 1 | Cy14b | H | H | Me | CF$_3$ | O |
| C.43b | H | 0 | 1 | Cy14b | H | H | Me | CF$_2$H | O |
| C.44b | H | 0 | 1 | Cy14b | H | Me | Me | CF$_3$ | O |
| C.45b | H | 0 | 1 | Cy14b | H | H | H | CF$_3$ | O |
| C.46b | H | 0 | 1 | Cy14b | H | Me | H | CF$_3$ | O |
| C.47b | H | 0 | 1 | Cy14b | H | Me | Me | Me | O |
| C.48b | H | 0 | 1 | Cy14b | H | Me | Me | H | O |
| C.49b | H | 0 | 1 | Cy15b | H | Me | Me | CF$_3$ | O |
| C.50b | H | 0 | 1 | Cy15b | H | H | Me | CF$_2$H | O |
| C.53b | H | 0 | 1 | Cy17b | H | H | Me | CF$_3$ | O |
| C.54b | H | 0 | 1 | Cy17b | H | H | Me | CF$_2$H | O |
| C.55b | H | 0 | 1 | Cy17b | H | Me | Me | CF$_3$ | O |
| C.56b | H | 0 | 1 | Cy17b | H | H | H | CF$_3$ | O |
| C.57b | H | 0 | 1 | Cy17b | H | Me | H | CF$_3$ | O |
| C.58b | H | 0 | 1 | Cy17b | H | Me | Me | Me | O |
| C.59b | H | 0 | 1 | Cy17b | H | Me | Me | H | O |
| C.60b | H | 0 | 1 | Cy18b | H | H | Me | CF$_2$H | O |
| C.61b | H | 0 | 1 | Cy18b | H | H | Me | CF$_3$ | O |
| C.62b | H | 0 | 1 | Cy19b | H | H | Me | CF$_3$ | O |
| C.63b | H | 0 | 1 | Cy19b | H | H | Me | CF$_2$H | O |
| C.64b | H | 0 | 1 | Cy19b | H | Me | Me | CF$_3$ | O |
| C.65b | H | 0 | 1 | Cy19b | H | H | H | CF$_3$ | O |
| C.66b | H | 0 | 1 | Cy19b | H | Me | H | CF$_3$ | O |
| C.67b | H | 0 | 1 | Cy19b | H | Me | Me | Me | O |
| C.68b | H | 0 | 1 | Cy19b | H | Me | Me | H | O |
| C.69b | H | 0 | 2 | Cy17b | H | H | Me | CF$_3$ | O |
| C.70b | H | 0 | 2 | Cy17b | H | H | Me | CF$_2$H | O |
| C.78b | H | 0 | 0 | Cy23b | Me$_3$Si | H | Me | CF$_3$ | O |
| C.79b | H | 0 | 1 | Cy24b | H | H | Me | CF$_2$H | O |
| C.80b | H | 0 | 1 | Cy24b | H | Me | Me | CF$_3$ | O |

Table 11a provides 80 compounds of formula (If) where $R^1$, m, n, Cy, $R^5$, $R^6$, $R^7$, Y and X are as defined in Table 11a.

Table 11b provides 38 compounds of formula (If) where $R^1$, m, n, Cy, $R^5$, $R^6$, $R^7$, Y and X are as defined in Table 11b.

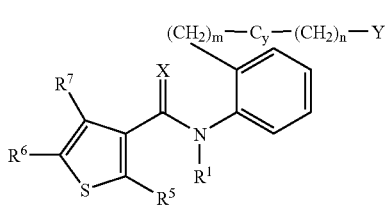

(If)

Table 12a provides 80 compounds of formula (Iff) where $R^1$, m, n, Cy, $R^5$, $R^6$, $R^7$, Y and X are as defined in Table 12a.

Table 12b provides 38 compounds of formula (Iff) where $R^1$, m, n, Cy, $R^5$, $R^6$, $R^7$, Y and X are as defined in Table 12b.

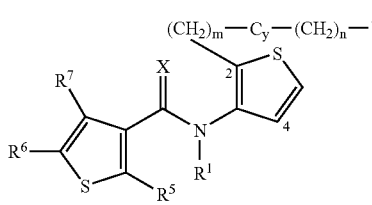

(Iff)

Table 13a provides 80 comnpounds of formula (Ig) where $R^1$, m, n, Cy, $R^5$, $R^6$, $R^7$, Y and X are as defined in Table 13a.

Table 13b provides 38 compounds of formula (Ig) where $R^1$, m, n, Cy, $R^5$, $R^6$, $R^7$, Y and X are as defined in Table 13b.

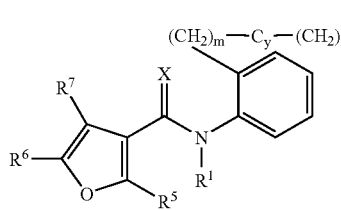

(Ig)

Table 14a provides 80 compounds of formula (Igg) where $R^1$, m, n, Cy, $R^5$, $R^6$, $R^7$, Y and X are as defined in Table 14a.

Table 14b provides 38 compounds of formula (Igg) where $R^1$, m, n, Cy, $R^5$, $R^6$, $R^7$, Y and X are as defined in Table 14b.

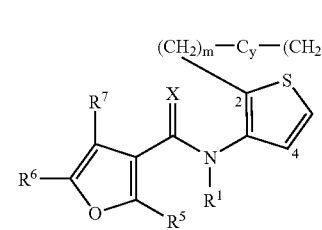

(Igg)

Table Da represents Table 15a (when D is 15), represents Table 16a (when D is 16), represents Table 17a (when D is 17), represents Table 18a (when D is 18), represents Table 19a (when D is 19) and represents Table 20a (when D is 20).

TABLE Da

| Compound No. | $R^1$ | m | n | Cy | Y | $R^5$ | X |
|---|---|---|---|---|---|---|---|
| D.1 | H | 0 | 0 | Cy1 | Me$_3$Si | CF$_3$ | O |
| D.2 | H | 0 | 0 | Cy1 | Me$_3$Si | Me | O |
| D.2 | H | 0 | 0 | Cy2 | Me$_3$Si | CF$_3$ | O |
| D.3 | H | 0 | 0 | Cy2 | Me$_3$Si | Me | O |
| D.4 | H | 0 | 0 | Cy2 | Me$_3$Si | CF$_2$Cl | O |
| D.5 | H | 0 | 0 | Cy2 | Me$_3$Si | CF$_3$ | S |
| D.7 | propargyl | 0 | 0 | Cy2 | Me$_3$Si | CF$_3$ | O |
| D.8 | allenyl | 0 | 0 | Cy2 | Me$_3$Si | CF$_3$ | O |
| D.9 | COCH$_3$ | 0 | 0 | Cy2 | Me$_3$Si | CF$_3$ | O |
| D.10 | H | 0 | 0 | Cy2 | Me$_3$Si | Me | S |
| D.11 | propargyl | 0 | 0 | Cy2 | Me$_3$Si | Me | O |
| D.12 | allenyl | 0 | 0 | Cy2 | Me$_3$Si | Me | O |
| D.13 | COCH$_3$ | 0 | 0 | Cy2 | Me$_3$Si | Me | O |
| D.14 | H | 1 | 0 | Cy2 | Me$_3$Si | CF$_3$ | O |
| D.15 | H | 1 | 0 | Cy2 | Me$_3$Si | Me | O |
| D.16 | H | 0 | 1 | Cy2 | Me$_3$Si | CF$_3$ | O |
| D.17 | H | 0 | 1 | Cy2 | Me$_3$Si | Me | O |
| D.18a | H | 0 | 0 | Cy3a | Me$_3$Si | CF$_3$ | O |

TABLE Da-continued

| Compound No. | R¹ | m | n | Cy | Y | R⁵ | X |
|---|---|---|---|---|---|---|---|
| D.19a | H | 0 | 0 | Cy3a | Me₃Si | Me | O |
| D.20 | H | 0 | 0 | Cy4 | Me₃Si | CF₃ | O |
| D.21 | H | 0 | 0 | Cy4 | Me₃Si | CF₂H | O |
| D.22 | H | 0 | 0 | Cy5 | Me₃Si | CF₃ | O |
| D.23 | H | 0 | 0 | Cy5 | Me₃Si | Me | O |
| D.24a | H | 0 | 0 | Cy6a | Me₃Si | CF₃ | O |
| D.25a | H | 0 | 0 | Cy6a | Me₃Si | Me | O |
| D.26 | H | 0 | 0 | Cy7 | Me₃Si | CF₃ | O |
| D.27 | H | 0 | 0 | Cy7 | Me₃Si | Me | O |
| D.28 | H | 0 | 0 | Cy8 | Me₃Si | CF₃ | O |
| D.29 | H | 0 | 0 | Cy8 | Me₃Si | Me | O |
| D.30a | H | 0 | 0 | Cy9a | Me₃Si | CF₃ | O |
| D.31a | H | 0 | 0 | Cy9a | Me₃Si | Me | O |
| D.32a | H | 0 | 0 | Cy10a | Me₃Si | CF₃ | O |
| D.33a | H | 0 | 0 | Cy10a | Me₃Si | Me | O |
| D.34 | H | 0 | 1 | Cy11 | H | CF₃ | O |
| D.35 | H | 0 | 1 | Cy11 | H | Me | O |
| D.36 | H | 0 | 1 | Cy12 | H | CF₃ | O |
| D.37 | H | 0 | 1 | Cy12 | H | Me | O |
| D.38 | H | 0 | 1 | Cy13 | H | CF₃ | O |
| D.39 | H | 0 | 1 | Cy13 | H | Me | O |
| D.40a | H | 0 | 1 | Cy14a | H | CF₃ | O |
| D.41a | H | 0 | 1 | Cy14a | H | Me | O |
| D.42a | propargyl | 0 | 1 | Cy14a | H | CF₃ | O |
| D.43a | allenyl | 0 | 1 | Cy14a | H | Me | O |
| D.44a | propargyl | 0 | 1 | Cy14a | H | Me | O |
| D.45a | allenyl | 0 | 1 | Cy14a | H | CF₃ | O |
| D.46a | H | 0 | 1 | Cy15a | H | CF₃ | O |
| D.47a | H | 0 | 1 | Cy15a | H | Me | O |
| D.48 | H | 0 | 1 | Cy16 | H | CF₃ | O |
| D.49 | H | 0 | 1 | Cy16 | H | Me | O |
| D.50a | H | 0 | 1 | Cy17a | H | CF₃ | O |
| D.51a | H | 0 | 1 | Cy17a | H | Me | O |
| D.52a | propargyl | 0 | 1 | Cy17a | H | CF₃ | O |
| D.53a | allenyl | 0 | 1 | Cy17a | H | Me | O |
| D.54a | propargyl | 0 | 1 | Cy17a | H | Me | O |
| D.55a | allenyl | 0 | 1 | Cy17a | H | CF₃ | O |
| D.56a | H | 0 | 1 | Cy18a | H | Me | O |
| D.57a | H | 0 | 1 | Cy18a | H | CF₃ | O |
| D.58a | H | 0 | 1 | Cy19a | H | CF₃ | O |
| D.59a | H | 0 | 1 | Cy19a | H | Me | O |
| D.60a | propargyl | 0 | 1 | Cy19a | H | CF₃ | O |
| D.61a | allenyl | 0 | 1 | Cy19a | H | Me | O |
| D.62a | propargyl | 0 | 1 | Cy19a | H | Me | O |
| D.63a | allenyl | 0 | 1 | Cy19a | H | CF₃ | O |
| D.64a | H | 0 | 2 | Cy17a | H | CF₃ | O |
| D.65a | H | 0 | 2 | Cy17a | H | Me | O |
| D.66 | H | 0 | 0 | Cy20 | Me₂SiCMe₃ | CF₃ | O |
| D.67 | H | 0 | 0 | Cy20 | Me₂SiCMe₃ | Me | O |
| D.68 | H | 0 | 1 | Cy20 | Me₃Si | CF₃ | O |
| D.69 | H | 0 | 1 | Cy20 | Me₃Si | Me | O |
| D.70 | H | 0 | 2 | Cy20 | Me₃Si | CF₃ | O |
| D.71 | H | 0 | 2 | Cy20 | Me₃Si | Me | O |
| D.72 | H | 0 | 0 | Cy21 | Me₃Si | CF₃ | O |
| D.73 | H | 0 | 0 | Cy21 | Me₃Si | Me | O |
| D.74 | H | 0 | 0 | Cy22 | Me₃Si | CF₃ | O |
| D.75 | H | 0 | 0 | Cy22 | Me₃Si | Me | O |
| D.76 | CHO | 0 | 0 | Cy22 | Me₃Si | CF₃ | O |
| D.77 | CHO | 0 | 0 | Cy22 | Me₃Si | Me | O |
| D.78a | H | 0 | 0 | Cy23a | Me₃Si | CF₃ | O |
| D.79a | H | 0 | 0 | Cy23a | Me₃Si | Me | O |
| D.80a | H | 0 | 1 | Cy24a | H | CF₃ | O |
| D.81a | H | 0 | 1 | Cy24a | H | Me | O |

Table Db represents Table 15b (when D is 15), represents Table 16b (when D is 16), represents Table 17b (when D is 17), represents Table 18b (when D is 18), represents Table 19b (when D is 19) and represents Table 20b (when D is 20).

TABLE Db

| Compound No. | R¹ | m | n | Cy | Y | R⁵ | X |
|---|---|---|---|---|---|---|---|
| D.18b | H | 0 | 0 | Cy3b | Me₃Si | CF₃ | O |
| D.19b | H | 0 | 0 | Cy3b | Me₃Si | Me | O |
| D.24b | H | 0 | 0 | Cy6b | Me₃Si | CF₃ | O |
| D.25b | H | 0 | 0 | Cy6b | Me₃Si | Me | O |
| D.30b | H | 0 | 0 | Cy9b | Me₃Si | CF₃ | O |
| D.31b | H | 0 | 0 | Cy9b | Me₃Si | Me | O |
| D.32b | H | 0 | 0 | Cy10b | Me₃Si | CF₃ | O |
| D.33b | H | 0 | 0 | Cy10b | Me₃Si | Me | O |
| D.40b | H | 0 | 1 | Cy14b | H | CF₃ | O |
| D.41b | H | 0 | 1 | Cy14b | H | Me | O |
| D.42b | propargyl | 0 | 1 | Cy14b | H | CF₃ | O |
| D.43b | allenyl | 0 | 1 | Cy14b | H | Me | O |
| D.44b | propargyl | 0 | 1 | Cy14b | H | Me | O |
| D.45b | allenyl | 0 | 1 | Cy14b | H | CF₃ | O |
| D.46b | H | 0 | 1 | Cy15b | H | CF₃ | O |
| D.47b | H | 0 | 1 | Cy15b | H | Me | O |
| D.50b | H | 0 | 1 | Cy17b | H | CF₃ | O |
| D.51b | H | 0 | 1 | Cy17b | H | Me | O |
| D.52b | propargyl | 0 | 1 | Cy17b | H | CF₃ | O |
| D.53b | allenyl | 0 | 1 | Cy17b | H | Me | O |
| D.54b | propargyl | 0 | 1 | Cy17b | H | Me | O |
| D.55b | allenyl | 0 | 1 | Cy17b | H | CF₃ | O |
| D.56b | H | 0 | 1 | Cy18b | H | Me | O |
| D.57b | H | 0 | 1 | Cy18b | H | CF₃ | O |
| D.58b | H | 0 | 1 | Cy19b | H | CF₃ | O |
| D.59b | H | 0 | 1 | Cy19b | H | Me | O |
| D.60b | propargyl | 0 | 1 | Cy19b | H | CF₃ | O |
| D.61b | allenyl | 0 | 1 | Cy19b | H | Me | O |
| D.62b | propargyl | 0 | 1 | Cy19b | H | Me | O |
| D.63b | allenyl | 0 | 1 | Cy19b | H | CF₃ | O |
| D.64b | H | 0 | 2 | Cy17b | H | CF₃ | O |
| D.65b | H | 0 | 2 | Cy17b | H | Me | O |
| D.78b | H | 0 | 0 | Cy23b | Me₃Si | CF₃ | O |
| D.79b | H | 0 | 0 | Cy23b | Me₃Si | Me | O |
| D.80b | H | 0 | 1 | Cy24b | H | CF₃ | O |
| D.81b | H | 0 | 1 | Cy24b | H | Me | O |

Table 15a provides 81 compounds of formula (Ih) where R¹, m, n, Cy, R⁵, Y and X are as defined in Table 15a.

Table 15b provides 36 compounds of formula (Ih) where R¹, m, n, Cy, R⁵, Y and X are as defined in Table 15b.

(Ih)

Table 16a provides 81 compounds of formula (Ihh) where R¹, m, n, Cy, R⁵, Y and X are as defined in Table 16a.

Table 16b provides 36 compounds of formula (Ihh) where R¹, m, n, Cy, R⁵, Y and X are as defined in Table 16b.

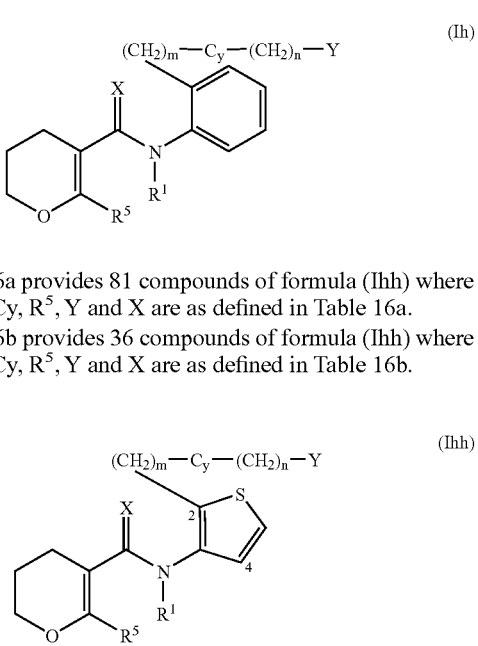

(Ihh)

Table 17a provides 81 compounds of formula (Ij) where $R^1$, m, n, Cy, $R^5$, Y and X are as defined in Table 17a.

Table 17b provides 36 compounds of formula (Ij) where $R^1$, m, n, Cy, $R^5$, Y and X are as defined in Table 17b.

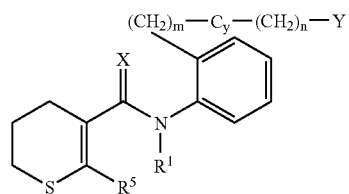

(Ij)

Table 18a provides 81 compounds of formula (Ijj) where $R^1$, m, n, Cy, $R^5$, Y and X are as defined in Table 18a.

Table 18b provides 36 compounds of formula (Ijj) where R, m, n, Cy, $R^5$, Y and X are as defined in Table 18b.

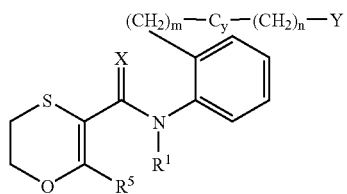

(Ijj)

Table 19a provides 81 compounds of formula (Ik) where $R^1$, m, n, Cy, $R^5$, Y and X are as defined in Table 19a.

Table 19b provides 36 compounds of formula (Ik) where $R^1$, m, n, Cy, $R^5$, Y and X are as defined in Table 19b.

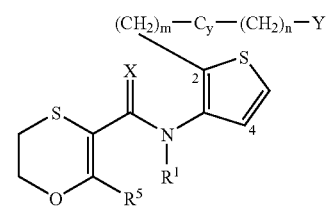

(Ik)

Table 20a provides 81 compounds of formula (Ikk) where $R^1$, m, n, Cy, $R^5$, Y and X are as defined in Table 20a.

Table 20b provides 36 compounds of formula (Ikk) where $R^1$, m, n, Cy, $R^5$, Y and X are as defined in Table 20b.

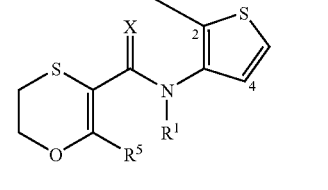

(Ikk)

Table Ea represents Table 21a (when E is 21), represents Table 22a (when E is 22), represents Table 23a (when E is 23), represents Table 24a (when E is 24), represents Table 25a (when E is 25) and represents Table 26a (when E is 26).

TABLE Ea

| Compound No. | $R^1$ | m | n | Cy | Y | $R^5$ | X |
|---|---|---|---|---|---|---|---|
| E.1 | H | 0 | 0 | Cy1 | Me$_3$Si | CF$_3$ | O |
| E.2 | H | 0 | 0 | Cy1 | Me$_3$Si | Cl | O |
| E.3 | H | 0 | 0 | Cy2 | Me$_3$Si | Cl | O |
| E.4 | H | 0 | 0 | Cy2 | Me$_3$Si | CF$_2$Cl | O |
| E.5 | H | 0 | 0 | Cy2 | Me$_3$Si | CF$_3$ | O |
| E.7 | propargyl | 0 | 0 | Cy2 | Me$_3$Si | CF$_3$ | O |
| E.8 | allenyl | 0 | 0 | Cy2 | Me$_3$Si | CF$_3$ | O |
| E.9 | COCH$_3$ | 0 | 0 | Cy2 | Me$_3$Si | CF$_3$ | O |
| E.10 | H | 0 | 0 | Cy2 | Me$_3$Si | Cl | S |
| E.11 | propargyl | 0 | 0 | Cy2 | Me$_3$Si | Cl | O |
| E.12 | allenyl | 0 | 0 | Cy2 | Me$_3$Si | Cl | O |
| E.13 | COCH$_3$ | 0 | 0 | Cy2 | Me$_3$Si | Cl | O |
| E.14 | H | 1 | 0 | Cy2 | Me$_3$Si | CF$_3$ | O |
| E.15 | H | 1 | 0 | Cy2 | Me$_3$Si | Cl | O |
| E.16 | H | 0 | 1 | Cy2 | Me$_3$Si | CF$_3$ | O |
| E.17 | H | 0 | 1 | Cy2 | Me$_3$Si | Cl | O |
| E.18a | H | 0 | 0 | Cy3a | Me$_3$Si | CF$_3$ | O |
| E.19a | H | 0 | 0 | Cy3a | Me$_3$Si | Cl | O |
| E.20 | H | 0 | 0 | Cy4 | Me$_3$Si | CF$_3$ | O |
| E.21 | H | 0 | 0 | Cy4 | Me$_3$Si | Cl | O |
| E.22 | H | 0 | 0 | Cy5 | Me$_3$Si | CF$_3$ | O |
| E.23 | H | 0 | 0 | Cy5 | Me$_3$Si | Cl | O |
| E.24a | H | 0 | 0 | Cy6a | Me$_3$Si | CF$_3$ | O |
| E.25a | H | 0 | 0 | Cy6a | Me$_3$Si | Cl | O |
| E.26 | H | 0 | 0 | Cy7 | Me$_3$Si | CF$_3$ | O |
| E.27 | H | 0 | 0 | Cy7 | Me$_3$Si | Cl | O |
| E.28 | H | 0 | 0 | Cy8 | Me$_3$Si | CF$_3$ | O |
| E.29 | H | 0 | 0 | Cy8 | Me$_3$Si | Cl | O |
| E.30a | H | 0 | 0 | Cy9a | Me$_3$Si | CF$_3$ | O |
| E.31a | H | 0 | 0 | Cy9a | Me$_3$Si | Cl | O |
| E.32a | H | 0 | 0 | Cy10a | Me$_3$Si | CF$_3$ | O |
| E.33a | H | 0 | 0 | Cy10a | Me$_3$Si | Cl | O |
| E.34 | H | 0 | 1 | Cy11 | H | CF$_3$ | O |
| E.35 | H | 0 | 1 | Cy11 | H | Cl | O |
| E.36 | H | 0 | 1 | Cy12 | H | CF$_3$ | O |
| E.37 | H | 0 | 1 | Cy12 | H | Cl | O |
| E.38 | H | 0 | 1 | Cy13 | H | CF$_3$ | O |
| E.39 | H | 0 | 1 | Cy13 | H | Cl | O |
| E.40a | H | 0 | 1 | Cy14a | H | CF$_3$ | O |
| E.41a | H | 0 | 1 | Cy14a | H | Cl | O |
| E.42a | propargyl | 0 | 1 | Cy14a | H | CF$_3$ | O |
| E.43a | allenyl | 0 | 1 | Cy14a | H | Cl | O |
| E.44a | propargyl | 0 | 1 | Cy14a | H | Cl | O |
| E.45a | allenyl | 0 | 1 | Cy14a | H | CF$_3$ | O |
| E.46a | H | 0 | 1 | Cy15a | H | CF$_3$ | O |
| E.47a | H | 0 | 1 | Cy15a | H | Cl | O |
| E.48 | H | 0 | 1 | Cy16 | H | CF$_3$ | O |
| E.49 | H | 0 | 1 | Cy16 | H | Cl | O |
| E.50a | H | 0 | 1 | Cy17a | H | CF$_3$ | O |
| E.51a | H | 0 | 1 | Cy17a | H | Cl | O |
| E.52a | propargyl | 0 | 1 | Cy17a | H | CF$_3$ | O |
| E.53a | allenyl | 0 | 1 | Cy17a | H | Cl | O |
| E.54a | propargyl | 0 | 1 | Cy17a | H | Cl | O |
| E.55a | allenyl | 0 | 1 | Cy17a | H | CF$_3$ | O |
| E.56a | H | 0 | 1 | Cy18a | H | Cl | O |
| E.57a | H | 0 | 1 | Cy18a | H | CF$_3$ | O |
| E.58a | H | 0 | 1 | Cy19a | H | CF$_3$ | O |
| E.59a | H | 0 | 1 | Cy19a | H | Cl | O |
| E.60a | propargyl | 0 | 1 | Cy19a | H | CF$_3$ | O |
| E.61a | allenyl | 0 | 1 | Cy19a | H | Cl | O |
| E.62a | propargyl | 0 | 1 | Cy19a | H | Cl | O |
| E.63a | allenyl | 0 | 1 | Cy19a | H | CF$_3$ | O |
| E.64a | H | 0 | 2 | Cy17a | H | CF$_3$ | O |
| E.65a | H | 0 | 2 | Cy17a | H | Cl | O |
| E.66 | H | 0 | 0 | Cy20 | Me$_2$SiCMe$_3$ | CF$_3$ | O |
| E.67 | H | 0 | 0 | Cy20 | Me$_2$SiCMe$_3$ | Cl | O |
| E.68 | H | 0 | 1 | Cy20 | Me$_3$Si | CF$_3$ | O |
| E.69 | H | 0 | 1 | Cy20 | Me$_3$Si | Cl | O |
| E.70 | H | 0 | 2 | Cy20 | Me$_3$Si | CF$_3$ | O |
| E.71 | H | 0 | 2 | Cy20 | Me$_3$Si | Cl | O |
| E.72 | H | 0 | 0 | Cy21 | Me$_3$Si | CF$_3$ | O |
| E.73 | H | 0 | 0 | Cy21 | Me$_3$Si | Cl | O |
| E.74 | H | 0 | 0 | Cy22 | Me$_3$Si | CF$_3$ | O |
| E.75 | H | 0 | 0 | Cy22 | Me$_3$Si | Cl | O |
| E.76 | CHO | 0 | 0 | Cy22 | Me$_3$Si | CF$_3$ | O |
| E.77 | CHO | 0 | 0 | Cy22 | Me$_3$Si | Cl | O |

TABLE Ea-continued

| Compound No. | R¹ | m | n | Cy | Y | R⁵ | X |
|---|---|---|---|---|---|---|---|
| E.78a | H | 0 | 0 | Cy23a | Me₃Si | CF₃ | O |
| E.79a | H | 0 | 0 | Cy23a | Me₃Si | Cl | O |
| E.80a | H | 0 | 1 | Cy24a | H | CF₃ | O |
| E.81a | H | 0 | 1 | Cy24a | H | Cl | O |
| E.82a | H | 0 | 2 | Cy17a | H | Cl | O |
| E.83a | H | 1 | 1 | Cy19a | H | Cl | O |

Table Eb represents Table 21b (when E is 21), represents Table 22b (when E is 22), represents Table 23b (when E is 23), represents Table 24b (when E is 24), represents Table 25b (when E is 25) and represents Table 26b (when E is 26).

TABLE Eb

| Compound No. | R¹ | m | n | Cy | Y | R⁵ | X |
|---|---|---|---|---|---|---|---|
| E.18b | H | 0 | 0 | Cy3b | Me₃Si | CF₃ | O |
| E.19b | H | 0 | 0 | Cy3b | Me₃Si | Cl | O |
| E.24b | H | 0 | 0 | Cy6b | Me₃Si | CF₃ | O |
| E.25b | H | 0 | 0 | Cy6b | Me₃Si | Cl | O |
| E.30b | H | 0 | 0 | Cy9b | Me₃Si | CF₃ | O |
| E.31b | H | 0 | 0 | Cy9b | Me₃Si | Cl | O |
| E.32b | H | 0 | 0 | Cy10b | Me₃Si | CF₃ | O |
| E.33b | H | 0 | 0 | Cy10b | Me₃Si | Cl | O |
| E.40b | H | 0 | 1 | Cy14b | H | CF₃ | O |
| E.41b | H | 0 | 1 | Cy14b | H | Cl | O |
| E.42b | propargyl | 0 | 1 | Cy14b | H | CF₃ | O |
| E.43b | allenyl | 0 | 1 | Cy14b | H | Cl | O |
| E.44b | propargyl | 0 | 1 | Cy14b | H | Cl | O |
| E.45b | allenyl | 0 | 1 | Cy14b | H | CF₃ | O |
| E.46b | H | 0 | 1 | Cy15b | H | CF₃ | O |
| E.47b | H | 0 | 1 | Cy15b | H | Cl | O |
| E.50b | H | 0 | 1 | Cy17b | H | CF₃ | O |
| E.51b | H | 0 | 1 | Cy17b | H | Cl | O |
| E.52b | propargyl | 0 | 1 | Cy17b | H | CF₃ | O |
| E.53b | allenyl | 0 | 1 | Cy17b | H | Cl | O |
| E.54b | propargyl | 0 | 1 | Cy17b | H | Cl | O |
| E.55b | allenyl | 0 | 1 | Cy17b | H | CF₃ | O |
| E.56b | H | 0 | 1 | Cy18b | H | Cl | O |
| E.57b | H | 0 | 1 | Cy18b | H | CF₃ | O |
| E.58b | H | 0 | 1 | Cy19b | H | CF₃ | O |
| E.59b | H | 0 | 1 | Cy19b | H | Cl | O |
| E.60b | propargyl | 0 | 1 | Cy19b | H | CF₃ | O |
| E.61b | allenyl | 0 | 1 | Cy19b | H | Cl | O |
| E.62b | propargyl | 0 | 1 | Cy19b | H | Cl | O |
| E.63b | allenyl | 0 | 1 | Cy19b | H | CF₃ | O |
| E.64b | H | 0 | 2 | Cy17b | H | CF₃ | O |
| E.65b | H | 0 | 2 | Cy17b | H | Cl | O |
| E.78b | H | 0 | 0 | Cy23b | Me₃Si | CF₃ | O |
| E.79b | H | 0 | 0 | Cy23b | Me₃Si | Cl | O |
| E.80b | H | 0 | 1 | Cy24b | H | CF₃ | O |
| E.81b | H | 0 | 1 | Cy24b | H | Cl | O |

Table 21a provides 83 compounds of formula (Im) where R¹, m, n, Cy, R⁵, Y and X are as defined in Table 21a.

Table 21b provides 36 compounds of formula (Im) where R¹, m, n, Cy, R⁵, Y and X are as defined in Table 21b.

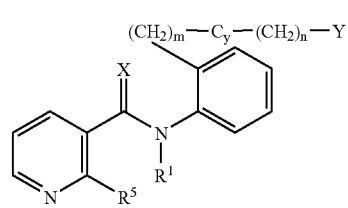

(Im)

Table 22a provides 83 compounds of formula (Imm) where R¹, m, n, Cy, R⁵, Y and X are as defined in Table 22a.

Table 22b provides 36 compounds of formula (Imm) where R¹, m, n, Cy, R⁵, Y and X are as defined in Table 22b.

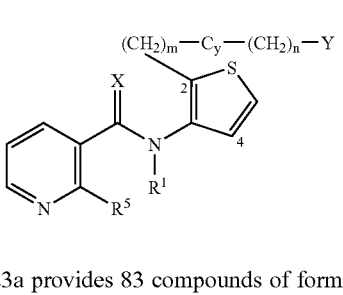

(Imm)

Table 23a provides 83 compounds of formula (In) where R¹, m, n, Cy, R⁵, Y and X are as defined in Table 23a.

Table 23b provides 36 compounds of formula (In) where R¹, m, n, Cy, R⁵, Y and X are as defined in Table 23b.

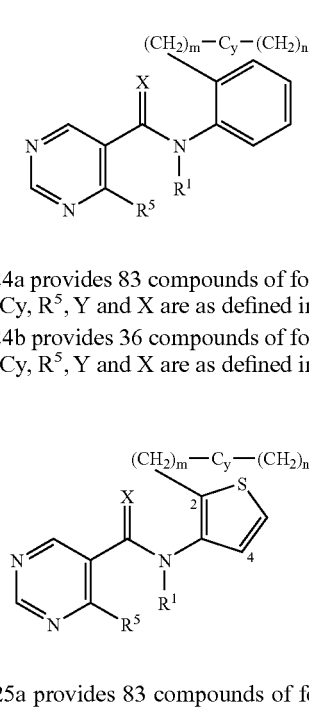

(In)

Table 24a provides 83 compounds of formula (Inn) where R¹, m, n, Cy, R⁵, Y and X are as defined in Table 24a.

Table 24b provides 36 compounds of formula (Inn) where R¹, m, n, Cy, R⁵, Y and X are as defined in Table 24b.

(Inn)

Table 25a provides 83 compounds of formula (Io) where R¹, m, n, Cy, R⁵, Y and X are as defined in Table 25a.

Table 25b provides 36 compounds of formula (Io) where R¹, m, n, Cy, R⁵, Y and X are as defined in Table 25b.

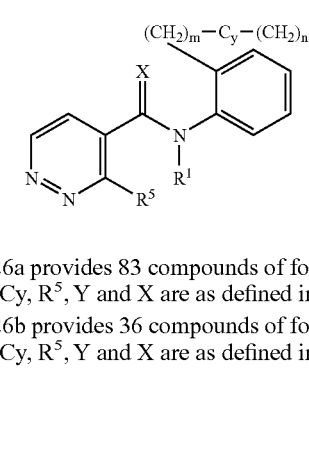

(Io)

Table 26a provides 83 compounds of formula (Ioo) where R¹, m, n, Cy, R⁵, Y and X are as defined in Table 26a.

Table 26b provides 36 compounds of formula (Ioo) where R¹, m, n, Cy, R⁵, Y and X are as defined in Table 26b.

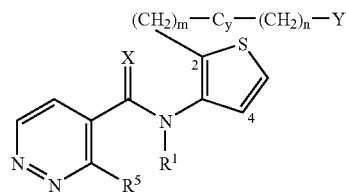

(Ioo)

Table 27a provides 72 compounds of formula (Ip) where m, n, Cy, $R^2$, $R^7$ and Y are as defined in Table 27a.

Table 27b provides 24 compounds of formula (Ip) where m, n, Cy, $R^2$, $R^7$ and Y are as defined in Table 27b.

TABLE 27a

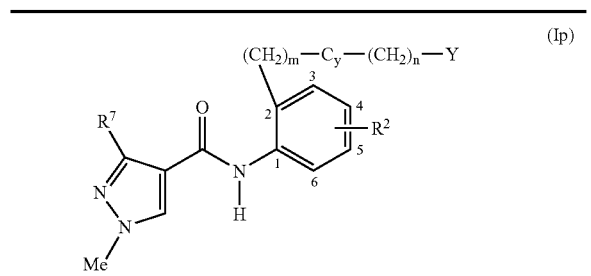

(Ip)

| Compound No. | $R^2$ | m | n | Cy | Y | $R^7$ |
|---|---|---|---|---|---|---|
| 27.1 | 3-F | 0 | 0 | Cy2 | Me$_3$Si | CF$_3$ |
| 27.2. | 4-F | 0 | 0 | Cy2 | Me$_3$Si | CF$_3$ |
| 27.3 | 5-F | 0 | 0 | Cy2 | Me$_3$Si | CF$_3$ |
| 27.4 | 6-F | 0 | 0 | Cy2 | Me$_3$Si | CF$_3$ |
| 27.5 | 3-F | 0 | 0 | Cy2 | Me$_3$Si | CF$_2$H |
| 27.6 | 4-F | 0 | 0 | Cy2 | Me$_3$Si | CF$_2$H |
| 27.7 | 5-F | 0 | 0 | Cy2 | Me$_3$Si | CF$_2$H |
| 27.8 | 6-F | 0 | 0 | Cy2 | Me$_3$Si | CF$_2$H |
| 27.9 | 3-Cl | 0 | 0 | Cy2 | Me$_3$Si | CF$_3$ |
| 27.10 | 4-Cl | 0 | 0 | Cy2 | Me$_3$Si | CF$_3$ |
| 27.11 | 5-Cl | 0 | 0 | Cy2 | Me$_3$Si | CF$_3$ |
| 27.12 | 6-Cl | 0 | 0 | Cy2 | Me$_3$Si | CF$_3$ |
| 27.13 | 3-Cl | 0 | 0 | Cy2 | Me$_3$Si | CF$_2$H |
| 27.14 | 4-Cl | 0 | 0 | Cy2 | Me$_3$Si | CF$_2$H |
| 27.15 | 5-Cl | 0 | 0 | Cy2 | Me$_3$Si | CF$_2$H |
| 27.16 | 6-Cl | 0 | 0 | Cy2 | Me$_3$Si | CF$_2$H |
| 27.17 | 3-Br | 0 | 0 | Cy2 | Me$_3$Si | CF$_3$ |
| 27.18 | 4-Br | 0 | 0 | Cy2 | Me$_3$Si | CF$_3$ |
| 27.19 | 5-Br | 0 | 0 | Cy2 | Me$_3$Si | CF$_3$ |
| 27.20 | 6-Br | 0 | 0 | Cy2 | Me$_3$Si | CF$_3$ |
| 27.21 | 3-Br | 0 | 0 | Cy2 | Me$_3$Si | CF$_2$H |
| 27.22 | 4-Br | 0 | 0 | Cy2 | Me$_3$Si | CF$_2$H |
| 27.23 | 5-Br | 0 | 0 | Cy2 | Me$_3$Si | CF$_2$H |
| 27.24 | 6-Br | 0 | 0 | Cy2 | Me$_3$Si | CF$_2$H |
| 27.25a | 3-F | 0 | 1 | Cy17a | H | CF$_3$ |
| 27.26a | 4-F | 0 | 1 | Cy17a | H | CF$_3$ |
| 27.27a | 5-F | 0 | 1 | Cy17a | H | CF$_3$ |
| 27.28a | 6-F | 0 | 1 | Cy17a | H | CF$_3$ |
| 27.29a | 3-F | 0 | 1 | Cy17a | H | CF$_2$H |
| 27.30a | 4-F | 0 | 1 | Cy17a | H | CF$_2$H |
| 27.31a | 5-F | 0 | 1 | Cy17a | H | CF$_2$H |
| 27.32a | 6-F | 0 | 1 | Cy17a | H | CF$_2$H |
| 27.33a | 3-Cl | 0 | 1 | Cy17a | H | CF$_3$ |
| 27.34a | 4-Cl | 0 | 1 | Cy17a | H | CF$_3$ |
| 27.35a | 5-Cl | 0 | 1 | Cy17a | H | CF$_3$ |
| 27.36a | 6-Cl | 0 | 1 | Cy17a | H | CF$_3$ |
| 27.37a | 3-Cl | 0 | 1 | Cy17a | H | CF$_2$H |
| 27.38a | 4-Cl | 0 | 1 | Cy17a | H | CF$_2$H |
| 27.39a | 5-Cl | 0 | 1 | Cy17a | H | CF$_2$H |
| 27.40a | 6-Cl | 0 | 1 | Cy17a | H | CF$_2$H |
| 27.41a | 3-Br | 0 | 1 | Cy17a | H | CF$_3$ |
| 27.42a | 4-Br | 0 | 1 | Cy17a | H | CF$_3$ |
| 27.43a | 5-Br | 0 | 1 | Cy17a | H | CF$_3$ |
| 27.44a | 6-Br | 0 | 1 | Cy17a | H | CF$_3$ |
| 27.45a | 3-Br | 0 | 1 | Cy17a | H | CF$_2$H |

TABLE 27a-continued

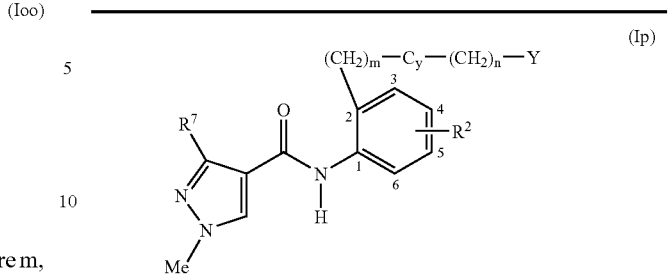

(Ip)

| Compound No. | $R^2$ | m | n | Cy | Y | $R^7$ |
|---|---|---|---|---|---|---|
| 27.46a | 4-Br | 0 | 1 | Cy17a | H | CF$_2$H |
| 27.47a | 5-Br | 0 | 1 | Cy17a | H | CF$_2$H |
| 27.48a | 6-Br | 0 | 1 | Cy17a | H | CF$_2$H |
| 27.49a | 3-F | 0 | 1 | Cy19a | H | CF$_3$ |
| 27.50a | 4-F | 0 | 1 | Cy19a | H | CF$_3$ |
| 27.51a | 5-F | 0 | 1 | Cy19a | H | CF$_3$ |
| 27.52a | 6-F | 0 | 1 | Cy19a | H | CF$_3$ |
| 27.53a | 3-F | 0 | 1 | Cy19a | H | CF$_2$H |
| 27.54a | 4-F | 0 | 1 | Cy19a | H | CF$_2$H |
| 27.55a | 5-F | 0 | 1 | Cy19a | H | CF$_2$H |
| 27.56a | 6-F | 0 | 1 | Cy19a | H | CF$_2$H |
| 27.57a | 3-Cl | 0 | 1 | Cy19a | H | CF$_3$ |
| 27.58a | 4-Cl | 0 | 1 | Cy19a | H | CF$_3$ |
| 27.59a | 5-Cl | 0 | 1 | Cy19a | H | CF$_3$ |
| 27.60a | 6-Cl | 0 | 1 | Cy19a | H | CF$_3$ |
| 27.61a | 3-Cl | 0 | 1 | Cy19a | H | CF$_2$H |
| 27.62a | 4-Cl | 0 | 1 | Cy19a | H | CF$_2$H |
| 27.63a | 5-Cl | 0 | 1 | Cy19a | H | CF$_2$H |
| 27.64a | 6-Cl | 0 | 1 | Cy19a | H | CF$_2$H |
| 27.65a | 3-Br | 0 | 1 | Cy19a | H | CF$_3$ |
| 27.66a | 4-Br | 0 | 1 | Cy19a | H | CF$_3$ |
| 27.67a | 5-Br | 0 | 1 | Cy19a | H | CF$_3$ |
| 27.68a | 6-Br | 0 | 1 | Cy19a | H | CF$_3$ |
| 27.69a | 3-Br | 0 | 1 | Cy19a | H | CF$_2$H |
| 27.70a | 4-Br | 0 | 1 | Cy19a | H | CF$_2$H |
| 27.71a | 5-Br | 0 | 1 | Cy19a | H | CF$_2$H |
| 27.72a | 6-Br | 0 | 1 | Cy19a | H | CF$_2$H |

TABLE 27b

| Compound No. | $R^2$ | m | n | Cy | Y | $R^7$ |
|---|---|---|---|---|---|---|
| 27.25b | 3-F | 0 | 1 | Cy17b | H | CF$_3$ |
| 27.26b | 4-F | 0 | 1 | Cy17b | H | CF$_3$ |
| 27.27b | 5-F | 0 | 1 | Cy17b | H | CF$_3$ |
| 27.28b | 6-F | 0 | 1 | Cy17b | H | CF$_3$ |
| 27.29b | 3-F | 0 | 1 | Cy17b | H | CF$_2$H |
| 27.30b | 4-F | 0 | 1 | Cy17b | H | CF$_2$H |
| 27.31b | 5-F | 0 | 1 | Cy17b | H | CF$_2$H |
| 27.32b | 6-F | 0 | 1 | Cy17b | H | CF$_2$H |
| 27.33b | 3-Cl | 0 | 1 | Cy17b | H | CF$_3$ |
| 27.34b | 4-Cl | 0 | 1 | Cy17b | H | CF$_3$ |
| 27.35b | 5-Cl | 0 | 1 | Cy17b | H | CF$_3$ |
| 27.36b | 6-Cl | 0 | 1 | Cy17b | H | CF$_3$ |
| 27.37b | 3-Cl | 0 | 1 | Cy17b | H | CF$_2$H |
| 27.38b | 4-Cl | 0 | 1 | Cy17b | H | CF$_2$H |
| 27.39b | 5-Cl | 0 | 1 | Cy17b | H | CF$_2$H |
| 27.40b | 6-Cl | 0 | 1 | Cy17b | H | CF$_2$H |
| 27.41b | 3-Br | 0 | 1 | Cy17b | H | CF$_3$ |
| 27.42b | 4-Br | 0 | 1 | Cy17b | H | CF$_3$ |
| 27.43b | 5-Br | 0 | 1 | Cy17b | H | CF$_3$ |
| 27.44b | 6-Br | 0 | 1 | Cy17b | H | CF$_3$ |
| 27.45b | 3-Br | 0 | 1 | Cy17b | H | CF$_2$H |
| 27.46b | 4-Br | 0 | 1 | Cy17b | H | CF$_2$H |
| 27.47b | 5-Br | 0 | 1 | Cy17b | H | CF$_2$H |
| 27.48b | 6-Br | 0 | 1 | Cy17b | H | CF$_2$H |

Table Fa represents Table 28a (when F is 28) and represents Table 29a (when F is 29).

TABLE Fa

| Compound No. | A | m | n | Cy | Y |
|---|---|---|---|---|---|
| F.1 | NH$_2$ | 0 | 0 | Cy1 | Me$_3$Si |
| F.2 | NH$_2$ | 0 | 0 | Cy2 | Me$_3$Si |
| F.3 | NO$_2$ | 0 | 0 | Cy2 | Me$_3$Si |
| F.4 | OSO$_2$CF$_3$ | 0 | 0 | Cy2 | Me$_3$Si |
| F.5 | N=CH(C$_6$H$_5$)$_2$ | 0 | 0 | Cy2 | Me$_3$Si |
| F.7 | Br | 0 | 0 | Cy2 | Me$_3$Si |
| F.18a | NH$_2$ | 0 | 0 | Cy3a | Me$_3$Si |
| F.19a | NO$_2$ | 0 | 0 | Cy3a | Me$_3$Si |
| F.20a | OSO$_2$CF$_3$ | 0 | 0 | Cy3a | Me$_3$Si |
| F.21 | NH$_2$ | 0 | 0 | Cy4 | Me$_3$Si |
| F.22 | NO$_2$ | 0 | 0 | Cy4 | Me$_3$Si |
| F.23 | OSO$_2$CF$_3$ | 0 | 0 | Cy4 | Me$_3$Si |
| F.24 | NH$_2$ | 0 | 0 | Cy5 | Me$_3$Si |
| F.25 | NO$_2$ | 0 | 0 | Cy5 | Me$_3$Si |
| F.26 | OSO$_2$CF$_3$ | 0 | 0 | Cy5 | Me$_3$Si |
| F.27 | N=CH(C$_6$H$_5$)$_2$ | 0 | 0 | Cy5 | Me$_3$Si |
| F.28a | NH$_2$ | 0 | 0 | Cy6a | Me$_3$Si |
| F.29a | NO$_2$ | 0 | 0 | Cy6a | Me$_3$Si |
| F.30a | OSO$_2$CF$_3$ | 0 | 0 | Cy6a | Me$_3$Si |
| F.31 | NH$_2$ | 0 | 0 | Cy7 | Me$_3$Si |
| F.32 | NO$_2$ | 0 | 0 | Cy7 | Me$_3$Si |
| F.33 | OSO$_2$CF$_3$ | 0 | 0 | Cy7 | Me$_3$Si |
| F.34 | N=CH(C$_6$H$_5$)$_2$ | 0 | 0 | Cy7 | Me$_3$Si |
| F.35 | NH$_2$ | 0 | 0 | Cy8 | Me$_3$Si |
| F.36 | NO$_2$ | 0 | 0 | Cy8 | Me$_3$Si |
| F.37 | OSO$_2$CF$_3$ | 0 | 0 | Cy8 | Me$_3$Si |
| F.38 | N=CH(C$_6$H$_5$)$_2$ | 0 | 0 | Cy8 | Me$_3$Si |
| F.39a | NH$_2$ | 0 | 0 | Cy9a | Me$_3$Si |
| F.40a | NH$_2$ | 0 | 0 | Cy10a | Me$_3$Si |
| F.41a | NO$_2$ | 0 | 0 | Cy10a | Me$_3$Si |
| F.42a | OSO$_2$CF$_3$ | 0 | 0 | Cy10a | Me$_3$Si |
| F.43a | N=CH(C$_6$H$_5$)$_2$ | 0 | 0 | Cy10a | Me$_3$Si |
| F.44 | NH$_2$ | 0 | 0 | Cy11 | H |
| F.45 | NO$_2$ | 0 | 1 | Cy11 | H |
| F.46 | NH$_2$ | 0 | 1 | Cy12 | H |
| F.47 | OSO$_2$CF$_3$ | 0 | 1 | Cy12 | H |
| F.48 | N=CH(C$_6$H$_5$)$_2$ | 0 | 1 | Cy12 | H |
| F.49 | NH$_2$ | 0 | 1 | Cy13 | H |
| F.50 | OSO$_2$CF$_3$ | 0 | 1 | Cy13 | H |
| F.51 | N=CH(C$_6$H$_5$)$_2$ | 0 | 1 | Cy13 | H |
| F.52a | NO$_2$ | 0 | 1 | Cy14a | H |
| F.53a | NH$_2$ | 0 | 1 | Cy14a | H |
| F.54a | OSO$_2$CF$_3$ | 0 | 1 | Cy14a | H |
| F.55a | N=CH(C$_6$H$_5$)$_2$ | 0 | 1 | Cy14a | H |
| F.56a | NH$_2$ | 0 | 1 | Cy15a | H |
| F.57a | OSO$_2$CF$_3$ | 0 | 1 | Cy15a | H |
| F.58a | N=CH(C$_6$H$_5$)$_2$ | 0 | 1 | Cy15a | H |
| F.59 | NH$_2$ | 0 | 1 | Cy16 | H |
| F.60 | OSO$_2$CF$_3$ | 0 | 1 | Cy16 | H |
| F.61 | N=CH(C$_6$H$_5$)$_2$ | 0 | 1 | Cy16 | H |
| F.62a | NO$_2$ | 0 | 1 | Cy17a | H |
| F.63a | NH$_2$ | 0 | 1 | Cy17a | H |
| F.64a | OSO$_2$CF$_3$ | 0 | 1 | Cy17a | H |
| F.65a | N=CH(C$_6$H$_5$)$_2$ | 0 | 1 | Cy17a | H |
| F.66a | NO$_2$ | 0 | 1 | Cy18a | H |
| F.67a | NH$_2$ | 0 | 1 | Cy18a | H |
| F.68a | OSO$_2$CF$_3$ | 0 | 1 | Cy18a | H |
| F.69a | N=CH(C$_6$H$_5$)$_2$ | 0 | 1 | Cy18a | H |
| F.70a | NO$_2$ | 0 | 1 | Cy19a | H |
| F.71a | NH$_2$ | 0 | 1 | Cy19a | H |
| F.72a | OSO$_2$CF$_3$ | 0 | 1 | Cy19a | H |
| F.73a | N=CH(C$_6$H$_5$)$_2$ | 0 | 1 | Cy19a | H |
| F.74 | NO$_2$ | 0 | 0 | Cy1 | Me$_3$Si |
| F.75 | OSO$_2$CF$_3$ | 0 | 0 | Cy1 | Me$_3$Si |
| F.76 | NO$_2$ | 0 | 0 | Cy21 | Me$_3$Si |
| F.77 | NH$_2$ | 0 | 0 | Cy21 | Me$_3$Si |
| F.78 | NO$_2$ | 0 | 0 | Cy22 | Me$_3$Si |
| F.79 | NH$_2$ | 0 | 0 | Cy22 | Me$_3$Si |
| F.80a | NO$_2$ | 0 | 0 | Cy23a | Me$_3$Si |
| F.81a | NH$_2$ | 0 | 0 | Cy23a | Me$_3$Si |
| F.82a | NH$_2$ | 0 | 1 | Cy24a | H |
| F.83a | NO$_2$ | 0 | 1 | Cy24a | H |
| F.84a | NH$_2$ | 1 | 1 | Cy19a | H |
| F.85a | NO$_2$ | 1 | 1 | Cy19a | H |
| F.86a | NH$_2$ | 0 | 2 | Cy17a | H |
| F.87a | NO$_2$ | 0 | 2 | Cy17a | H |
| F.88 | OSO$_2$CF$_3$ | 0 | 1 | Cy2 | H |
| F.89 | N=CH(C$_6$H$_5$)$_2$ | 0 | 1 | Cy2 | H |
| F.90 | NH$_2$ | 0 | 1 | Cy2 | H |

Table Fb represents Table 28b (when F is 28) and represents Table 29b (when F is 29).

TABLE Fb

| Compound No. | A | m | n | Cy | Y |
|---|---|---|---|---|---|
| F.18b | NH$_2$ | 0 | 0 | Cy3b | Me$_3$Si |
| F.19b | NO$_2$ | 0 | 0 | Cy3b | Me$_3$Si |
| F.20b | OSO$_2$CF$_3$ | 0 | 0 | Cy3b | Me$_3$Si |
| F.28b | NH$_2$ | 0 | 0 | Cy6b | Me$_3$Si |
| F.29b | NO$_2$ | 0 | 0 | Cy6b | Me$_3$Si |
| F.30b | OSO$_2$CF$_3$ | 0 | 0 | Cy6b | Me$_3$Si |
| F.39b | NH$_2$ | 0 | 0 | Cy9b | Me$_3$Si |
| F.40b | NH$_2$ | 0 | 0 | Cy10b | Me$_3$Si |
| F.41b | NO$_2$ | 0 | 0 | Cy10b | Me$_3$Si |
| F.42b | OSO$_2$CF$_3$ | 0 | 0 | Cy10b | Me$_3$Si |
| F.43b | N=CH(C$_6$H$_5$)$_2$ | 0 | 0 | Cy10b | Me$_3$Si |
| F.52b | NO$_2$ | 0 | 1 | Cy14b | H |
| F.53b | NH$_2$ | 0 | 1 | Cy14b | H |
| F.54b | OSO$_2$CF$_3$ | 0 | 1 | Cy14b | H |
| F.55b | N=CH(C$_6$H$_5$)$_2$ | 0 | 1 | Cy14b | H |
| F.56b | NH$_2$ | 0 | 1 | Cy15b | H |
| F.57b | OSO$_2$CF$_3$ | 0 | 1 | Cy15b | H |
| F.58b | N=CH(C$_6$H$_5$)$_2$ | 0 | 1 | Cy15b | H |
| F.62b | NO$_2$ | 0 | 1 | Cy17b | H |
| F.63b | NH$_2$ | 0 | 1 | Cy17b | H |
| F.64b | OSO$_2$CF$_3$ | 0 | 1 | Cy17b | H |
| F.65b | N=CH(C$_6$H$_5$)$_2$ | 0 | 1 | Cy17b | H |
| F.66b | NO$_2$ | 0 | 1 | Cy18b | H |
| F.67b | NH$_2$ | 0 | 1 | Cy18b | H |
| F.68b | OSO$_2$CF$_3$ | 0 | 1 | Cy18b | H |
| F.69b | N=CH(C$_6$H$_5$)$_2$ | 0 | 1 | Cy18b | H |
| F.70b | NO$_2$ | 0 | 1 | Cy19b | H |
| F.71b | NH$_2$ | 0 | 1 | Cy19b | H |
| F.72b | OSO$_2$CF$_3$ | 0 | 1 | Cy19b | H |
| F.73b | N=CH(C$_6$H$_5$)$_2$ | 0 | 1 | Cy19b | H |
| F.80b | NO$_2$ | 0 | 0 | Cy23b | Me$_3$Si |
| F.81b | NH$_2$ | 0 | 0 | Cy23b | Me$_3$Si |
| F.82b | NH$_2$ | 0 | 1 | Cy24b | H |
| F.83b | NO$_2$ | 0 | 1 | Cy24b | H |

Table 28a provides 90 compounds of formula (IIa) where A, m, n, Cy and Y are as defined in Table 28a.

Table 28b provides 34 compounds of formula (IIa) where A, m, n, Cy and Y are as defined in Table 28b.

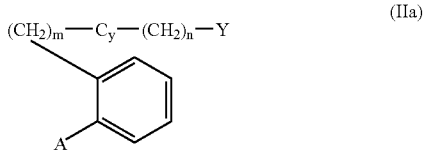

(IIa)

Table 29a provides 90 compounds of formula (IIb) where A, m, n, Cy and Y are as defined in Table 29a.

Table 29b provides 34 compounds of formula (IIb) where A, m, n, Cy and Y are as defined in Table 29b.

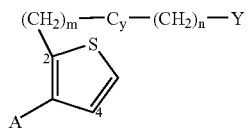

Throughout this description, temperatures are given in degrees Celsius; "NMR" means nuclear magnetic resonance spectrum; MS stands for mass spectrum; "%" is percent by weight, unless corresponding concentrations are indicated in other units; and specific rotations are given in degrees at the wavelength of the sodium line and are quoted at a specific concentration, c, the solvent being tetrahyrdofuran unless otherwise specified.

The following abbreviations are used throughout this description:

m.p.=melting point
s=singlet
d=doublet
t=triplet
m=multiplet
qd=quartet of doublets
b.p.=boiling point.
br=broad
dd=doublet of doublets
q=quartet
ppm=parts per million
sext=sextet Table 30 shows selected melting point and selected NMR data all with $CDCl_3$ as the solvent (unless otherwise stated; if a mixture of solvents is present, this is indicated as, for example, $(CDCl_3/d_6\text{-DMSO})$) and characteristic mass spectrum signals (no attempt is made to list all characterising data in all cases) for compounds of Tables 1 to 29.

TABLE 30

| Compound Number | $^1$H-NMR data: (ppm/multiplicity/number of Hs) or mass spectrum signal | m.p./(° C.) |
|---|---|---|
| 1.3 | | 107-111 |
| 1.4 | 0.0(s, 9); 0.25(m, 1); 0.7(m, 1); 0.9(m, 1); 1.7(m, 1); 3.95(s, 3); 6.85(t, 1); 7.05(m, 2), 7.2(m, 2); 8.0(s, 1); 8.1(d, 1), 8.35(s, 1). | 94-95 |
| 1.4A - see Example 7 | 0.0(s, 9); 0.25(m, 1); 0.7(m, 1); 0.9(m, 1); 1.7(m, 1); 3.95(s, 3); 6.85(t, 1); 7.05(m, 2), 7.2(m, 2); 8.0(s, 1); 8.1(d, 1), 8.35(s, 1). | oil |
| 1.4B - see Example 7 | 0.0(s, 9); 0.25(m, 1); 0.7(m, 1); 0.9(m, 1); 1.7(m, 1); 3.95(s, 3); 6.85(t, 1); 7.05(m, 2), 7.2(m, 2); 8.0(s, 1); 8.1(d, 1), 8.35(s, 1). | oil |
| 1.12 | −0.18(s, 1.5); 0.0(s, 1.5); 0.0-0.2(m, 1); 0.7(m, 0.5); 0.8(m, 0.5); 0.95(m, 1); 1.8(m, 1); 2.3(m, 1); 3.65(s, 3); 4.2-4.35 and 4.8-4.95(m, 2); 5.85(s, 0.5); 5.95(s, 0.5); 6.9-7.6(m, 5). | |
| 1.13 | −0.18(s, 1.5); 0.0(s, 1.5); −0.1-0.2(m, 1); 0.75(m, 1); 0.9(m, 0.5); 1.0(m0.5); 1.75(m, 1); 3.7(s, 3); 5.1(m, 2); 5.75(s, 0.5); 5.9(s, 0.5); 6.9-7.6(m, 5); 7.85(t, 1). | |
| 1.27 | Mass spectrum: 378(M+1; corresponds to M+H$^+$); 441(M+64; corresponds to M+MeCN+Na$^+$) | |
| 1.60a | | 132-135 |
| 1.61a | | 117-119 |
| 1.63a | Mass spectrum 416(M+1; corresponds to M+H$^+$). | |
| 1.78a | | 140-141 |
| 1.84 | | 119-121 |
| 1.85 | | 131-133 |
| 1.94a | | 74-77 |
| 1.96a | 0.0(d, 3); 0.4-2.1(m, 13); 2.9(m, 1); 3.9(s, 3); 6.85(t, 1); 7.1-7.2(m, 2); 7.3(m, 1); 7.6(br.1); 7.8(br.1); 8.0(br.1) | |
| 1.98a | 0.0(s, 3); 0.05(s, 3); 0.45(m, 2); 0.75(m, 2); 1.2-2.0(m, 5); 2.55(d, 2); 4.0(s, 3); 6.9(t, 1); 7.1-7.3(m, 3); 7.9-8.0(m, br, 2); 8.1(br.s, 1) | |
| 3.3 | 0.0(s, 9); 0.22(m, 1); 0.7(m, 1); 1.8(m, 1); 7.15(m, 2), 7.3(m, 1); 7.45(m, 1); 8.2(d, 1); 8.3(d, 1); 8.55(broad s+m, 2). | |
| 5.3 | | 61-64 |
| 5.60a | | 118-119 |
| 13.3 | | 98-99 |
| 21.3 | 0.0(s, 9); 0.22(m, 1); 0.9(m, 2); 0.9(m, 1); 1.7(m, 1); 3.72(s, 3); 6.95(s, 1); 7.05(m, 2), 7.2(m, 1), 7.3(s, 1); 8.05(broad s, 1); 8.15(d, 1). | |
| 21.51a | | 88-92 |
| 28.2 | −0.1(m, 1); 0.0(s, 9); 0.75(m, 2), 1.6(m, 1); 3.95(broad, 2); 6.65(m, 2); 7.0(m, 2). | |
| 28.4 | 0.0(s, 9); 0.1(m, 2); 0.9(m, 1); 2.0(m, 1), 6.9(d, 1); 7.2(m, 3). | |
| 28.5 | 0.0(s, 9); 0.1(m, 1); 0.9(m, 1); 1.1(m, 1); 2.0(m, 1); 6.5(m, 1); 6.9(m, 3); 7.2(m, 2); 7.3(m, 3); 7.5(m, 3); 7.9(d, 2). | |
| 28.24a | Mass spectrum: 234(M+1; corresponds to M+H$^+$); 275(M+42; corresponds to M+MeCN+H$^+$). | |
| 28.63a | 0.0(s, 3); 0.1(s, 3); 0.45(t of d, 1); 0.7(t, 2); 0.9(m, 1); 1.2(m, 1); 1.5(m, 1); 1.85(m, 1); 2.1(m, 1), 2.5(m, 1); 3, 65(broad s, 2); 6.65(d, 1); 6.75(t, 1); 6.95(t, 1); 7.1(d, 1). | |
| 28.82a | 0.0(s, 6); 0.6(m, 2); 1.8(m, 2): 2.2(m, 2); 3.9(very broad s, 2); 5.6(s, 1); 6.6(m, 1); 6.85(m, 1); 6.95(m, 1). | |
| 28.83a | 0.0(s, 6); 0.6(m, 2); 1.8(m, 2): 2.2(m, 2); 5.4(s, 1); 7.15-7.8(m, 4). | |
| 28.86a | −0.1(s, 1.5); 0.0(s, 1.5); 0.4-2.1(m, 13); 2.6(m, 1); 3.4(br, 2); 6.6(d, 1); 6.7(t, 1); 6.9(t, 1); 7.1(d, 1). | |
| 28.88 | | Yellow oil |

TABLE 30-continued

| Compound Number | $^1$H-NMR data: (ppm/multiplicity/number of Hs) or mass spectrum signal | m.p./(° C.) |
|---|---|---|
| 28.89 | Mass spectrum: 384(M+1; corresponds to M+H$^+$). | Yellow oil |
| 28.90 | Mass spectrum: 220(M+1; corresponds to M+H$^+$). | Yellow oil |

The compounds according to the present invention may be prepared according to the following reaction schemes, in which, unless otherwise stated, the definition of each variable is as defined above for a compound of formula (I).

There are a number of alternative methods for preparing a compound of formula (I).

Method A

A compound of formula (I) may be prepared by reacting a compound of formula (II) [in which A is NH$_2$, NHCH(O), optionally substituted (C$_{1-4}$)alkylC(=O)NH or optionally substituted (C$_{1-4}$)alkylOC(=O)NH] with a compound of formula Het-C(=O)OR' [where R' is C$_{1-5}$ alkyl] in the presence of a strong base [for example NaH or sodium hexamethyldisilazane], in a dry polar solvent [preferably THF] and at a temperature between −10° C. and the boiling point of the solvent [preferably at ambient temperature]. The article by J. Wang et al [Synlett 2001, 1485] provides details of analogous preparations. When A is NHCH(O), optionally substituted (C$_{1-4}$)alkylC(=O)NH or optionally substituted (C$_{1-4}$)alkylOC(=O)NH; and a compound of formula (I) in which R$^1$ is H is desired, then hydrolysis according to Method E below must follow.

Method B

A compound of formula (I) may be prepared by reacting a compound of formula (II) [where A is as defined above in Method A] with a compound of formula Het-C(=O)R" [where R" is OH or a leaving group, such as Cl, Br, F or OC(=O)C$_{1-4}$ alkyl] in an inert organic solvent [such as ethylacetate, dichloromethane, dioxane, THF or DMF] and at a temperature between −10° C. and the boiling point of the sol-vent [preferably at ambient temperature]. If R" is OH, then the reaction is carried out in the presence of an activating agent [for example BOP—Cl] and two equivalents of a base [such as a tertiary amine, an inorganic carbonate or a hydrogen carbonate]. Alternatively, if R" is a leaving group, then the reaction is carried out in the presence of at least one equivalent of base [for example pyridine, a tertiary amine, an inorganic carbonate or a hydrogen carbonate; a stronger base, such as NaH or sodium hexamethyldisilazane is used when A is NHCH(O), optionally substituted (C$_{1-4}$)alkylC(=O)NH or optionally substituted (C$_{1-4}$)alkylOC(=O)NH]. If a compound of formula (I) in which R$^1$ is H is desired, then hydrolysis according to Method E must follow.

Method C

A compound of formula (I) [where R$^1$ is as defined above but is not hydrogen] may be prepared by reacting a compound of formula (I) [where R$^1$ is hydrogen] with a compound of formula R$^1$-L$^1$ [where R$^1$ is as defined above but is not hydrogen; and L$^1$ is a leaving group, such as Cl, Br, I, a sulfonate (for example a mesylate or a tosylate) or OC(O)C$_{1-4}$ alkyl] in a solvent [such as an halogenated solvent (for example dichloromethane), an ether, ethylacetate, DMF or even water (as a biphasic mixture, optionally in the presence of a phase transfer catalyst such as tetrabutylammonium hydrogensulfate)] and in the presence of a base [such as a tertiary amine, an alkali carbonate, an alkali bicarbonate, an alkali hydroxide or NaH; though when L$^1$ is O(CO)C$_{1-4}$alkyl then simply heating without base is possible].

Method D

A compound of formula (I) may be prepared by reacting a compound of formula (II) [where A is halogen, preferably bromo or iodo] with a compound of formula Het-C(=O)NH$_2$ in the presence of a Cu(I) compound and an aprotic solvent [such as a cyclic ether, for example dioxane] at an elevated temperature and preferably at reflux. It is preferred that CuI is used at 2% to 100% mole/mole, relative to the compound of formula (II), in the presence of a 1,2-diamine (such as 1,2-diamino cyclohexane or ethylene diamine) as a ligand-forming substance and at least one equivalent of a base (such as an alkali carbonate or an alkali phosphate). The article by A. Klapars et al. J. Am. Chem. Soc. 123, 7727 (2001) provides details of analogous preparations.

Method E

A compound of formula (I) [where R$^1$ is H] may be prepared from a compound of formula (I) [where R$^1$ is as defined above, but is not H] by acidic or alkaline hydrolysis. For this purpose the, compound is treated with aqueous acid or base, for example HCl, HBr or an organic hydroxide [such as sodium-, potassium-, calcium- or barium-hydroxide] in an appropriate solvent which is preferably mixable with water [for example TIF, dioxane, a lower alcohol or water itself] at ambient or elevated temperatures.

Method F

A compound of formula (I) [where R$^1$ is H] may be prepared from a compound of formula (II) [where A is N=C (C$_6$H$_5$)$_2$] by converting A to NH$_2$, for example according to methods described by J. Ahman et al. Tetrahedron Letters 38, 6363 (1997) and proceeding according to Method A or Method B, preferably without isolation or purification of the intermediates.

Many compounds of formula (III) or (IV) (R$^3$ as defined above) which do not have additional substituents on the benzene or thiophene ring, have been described in the literature.

(III)

(IV)

A compound of formula (II) may be prepared either by introducing the appropriate functionality A' into a compound of formula (III) or (IV) and transforming it if necessary to the desired function A. Alternatively, and preferentially, a compound of formula (II) may be prepared by methods analogous to the literature methods for the preparation of compounds (III) and (IV) where the starting materials already have the appropriate substituent A' in place; these compounds are referred to as (IIIa) and (IVa). Often the reaction conditions and stoichiometry of the reagents must be modified to accommodate the additional substituent A'. Afterwards, A' (if desired) is converted to A according to known methodology to give a compound of formula (II). The preferred synthetic strategy is depicted in the following schemes and is further described below:

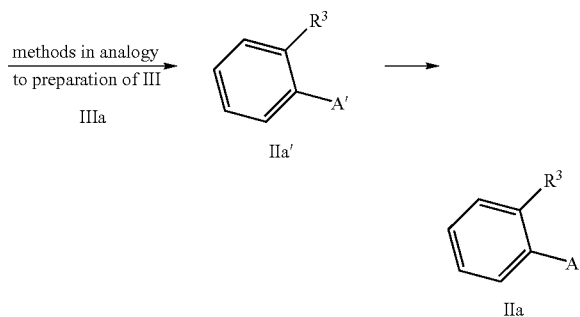

Step 1:

Some suitable methods for the preparation of a compound of formula (III) which can be used under modified conditions with the appropriate starting materials for the preparation of a compound of formula (IIa') are described in the following documents:

J. Org. Chem. 65, 8919 (2000); Tetrahedron 49, 8487 (1993); J. Org. Chem. 51, 2206 (1986), J. Org. Chem. 56, 3109 (1991); Acta chem. Scand. 53, 493 (1999); J. Am. Chem. Soc. 123, 10899 (2001); Org. Lett. 4, 2225 (2002); Tetrahedron 57, 2847 (2001);.Tetrahedron Letters 42, 6137 (2001); Tetrahedron Letters 36, 3119 (1995); EP 696592; EP 713878; FR 2689893; Bull. Chem. Soc. Jpn. 64, 1461 (1991); WO9214692; J. Org. Chem. 67, 6869 (2002); Pesticide Science 52, 138 (1998); Izv. Akad. Nauk, Ser. Khim. 1996, 955; 1995,2475; ); Tetrahedron Letters 33, 2295 (1992); Organometallics 11, 1428 (1992); 10, 528 (1991); Ann. Chem. 1979, 1915; J. Orgmet. Chem.341, 133 (1988); Zeitschrift f. Anorg. Allg. Chem. 459, 37 (1979); Tetrahedron Letters 22, 4449 (1981); U.S. Pat. No. 3,125,637; J. Org. Chem. 65, 3135 (2000).

A' is a group A, as defined above, or a precursor group of A, which is compatible with the reaction conditions of step 1 and which can be converted to A by known chemical methodology. Especially valuable precursor groups are free and protected OH and protected amino groups. References to useful protecting groups for phenoles and anilines are given e.g. in T. W. Green and P. G. M. Wuts, Protective Groups in Organic Synthesis 3$^{rd}$ edition p. 503-614 (Wiley 1999).

Step2: According to the nature of A', a compound of formula (IIa') may be converted to a compound of formula (IIa) (where A=NH$_2$) [for example by catalytic hydrogenation or chemical reduction (A' is nitro) or deprotection (A' is protected amino group)]. A compound of formula (IIa) (A=OSO$_2$CF$_3$) may be prepared by deprotection of the protected OH (if A' is protected OH) and converting he resultant compound of formula (IIa') (A=OH) to a triflate with triflic anhydride and a suitable base. A compound of formula (IIa) (A is OSO$_2$CF$_3$ or Halogen) may in a further step be converted to a compound of formula (IIa) (A=NH$_2$) by using methodologies described by J. Ahman et al. Tetrahedron Letters 38, 6363 (1997) and X. Huang et al., Org. Lett. 3, 3417 (2001) and references cited therein.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I),can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later, for example from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc. The compounds of formula (I) are, for example, effective against the phytopathogenic fungi of the following classes: Fungi imperfecti (e.g. Botrytis, Pyricularia, Helminthosporium, Fusarium, Septoria, Cercospora and Alternaria) and Basidiomycetes (e.g. Rhizoctonia, Hemileia, Puccinia). Additionally, they are also effective against the Ascomycetes classes (e.g. Venturia and Erysiphe, Podosphaera, Monilinia, Uncinula) and of the Oomycetes classes (e.g. Phytophthora, Pythium, Plasmopara). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO97/33890.

The compounds of formula (I) are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) can be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenlconazole, ipconazole, metconazole, myclobutanil, pefurazoate, penconazole, pyrifenox, prochloraz, propiconazole, simeconazole, tebuconazole, tetraconazole, triadimefon, triadinenol, triflumizole, triticonazole; pyrimidinyl carbinole, such as ancymidol, fenarimol, nuarimol; 2-amino-pymidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydro-phthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencaxb, dimethomorph, SYP-LI90 proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formnula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

EXAMPLE 1

This Example illustrates the preparation of Compound Numbers 28.83a, 28.63a and 1.61a.

Step A: 1,1-Dimethyl-3-(2'-nitro)phenyl-silacyclohexene-2 [Compound 28.83a]

2-Nitro-phenylacetylene (prepared according to Synthesis 1980, 627) (25 g), 1,1-dimethy-1-silacyclobutane (21.9 ml) and $PdCl_2((Ph_3P)_2$ (9.5g) were refluxed in 450 ml dry toluene under an atmosphere of nitrogen for 3 hours. After cooling to room temperature the solvent was evaporated and the residue (51.8 g) was chromatographed over 1.3 kg of silica gel (eluent: hexane:ethylacetate::39:1). An olive green oil (19.9 g) was isolated, which contained (according to mr) 60% of Compound 28.83a. This material was used directly in the next step.

Step B: 1,1-Dimethyl-3-(2'-amino)phenyl-silacyclohexane [Compound 28.63a]

The product of step A was hydrogenated in TBF over Pd (10% on carbon) at athmospheric pressure and room temperature. Filtration of the catalyst, evaporation of the solvent and chromatography over silica gel (eluent: hexane:ethylacetate:: 19:1) yielded Compound 28.63a (5.75 g).

Step C: Compound Number 1.61a

Compound Number 28.63a (0.17 g) was dissolved in TBF (5 ml). N-Methyl-3-difluoromethyl-4-chlorocarbonyl-pyrazole (0.15 g) was added and then pyridine (0.062 ml) was added while cooling with ice. The resultant white suspension was stirred overnight, poured on to water, extracted with ethyl acetate and dried over sodium sulfate. The solvent was evaporated and the residue (0.3 g) chromatographed on silica gel (eluent: hexane:ethyl acetate::2:1) to yield Compound Number 1.61a (0.26 g) melting at 117-119° C.

An analogous reaction sequence [but starting from 1-methyl-1-ethyl-silacyclobutane or 1-methyl-1-ethenyl-silycyclobutane instead of 1,1-dimethy-1-silacyclobutane] was used to prepare Compound Numbers 28.87a, 28.86a and 1.96a.

EXAMPLE 2

This Example illustrates the preparation of Compound Numbers 28.82a, and 1.94a.

Step A: 1,1-Dimethyl-3-(2'-amino)phenyl-silacyclohexene-2 [Compound 28.82a]

The product from Example 1 step A (1.5 g) was dissolved in ethanol (50 ml; 50% by volume) to which powdered iron (1.5 g) was added. The resultant suspension was heated to reflux. At this temperature HCl (0.35 ml; 2N), dissoved in ethanol (3.5 ml, 50% by volume) was added over 10 minutes and the resultant mixture was refluxed overnight. After cooling to room temperature, the suspension was filtered, neutralised with bicarbonate, extracted with ethyl acetate and dried with sodium sulfate. Evaporation of the solvent and chromatopgraphy on silica gel (eluent: hexane:ethyl acetate::9:1) yielded Compound 28.82a (0.14 g).

2-Amino-styrene (0.06 g) and 1-allyl-dimethylsilyl-2-(2'aminophenyl)-ethene (0.12 g) were also isolated, as side products.

Step B: Compound 1.94a

This compound was prepared from 1,1-dimethyl-3-(2'-amino)phenyl-silacyclohexene-2 [Compound 28.83a] (0.12 g) and N-methyl-3-trifluoromethyl-4-chlorocarbonyl-pyrazole (0.12 g) as described in Example 1 step C. The yield was 0.17 g of off-white crystals, melting at.74-77° C.

EXAMPLE 3

This Example illustrates the preparation of Compound Numbers 28.4, 28.5, 28.2 and 5.3.

Step A: Trans-1-(2'trifluormethylsulfonyloxy-phenyl)-2-trimethylsilyl-cycloproane [Compound 28.4]

Trans-1-(hydroxy-phenyl)-2-trimethylsilyl-cyclopropane (2.9 g) [prepared according to Org. Letters 4, 2225 (2002)] in pyridine (15 ml) was treated at 0-5° C. with triflic anhydride (2.55 ml). The mixture was first stirred for 90 minutes at this temperature and then for another 90 minutes at room temperature. Work-up with water, extraction with ethyl acetate, drying over sodium sulfate, removal of the solvent and chromatography on silica gel (eluent: hexane:ethyl acetate::19:1) yielded Compound 28.4 (4.4 g) which was used for the next-step.

Step B: Trans-1-(2'-diphenylmethyleneimino-phenyl)-2-trimethylsilyl-cyclopropane [Compound 28.5]

Dry THF (40 ml) was carefully degassed by bubbling in nitrogen for 15 minutes. Under a nitrogen atmosphere, palladiumdiacetate (0.1 5 g), rac.BhAP (0.65 g) and benzophenonimine (2.3 ml) were added sequentially. After stirring for 30 minutes at room temperature cesiumcarbonate (5.1 g) was added and the mixture was refluxed overnight. After cooling, the suspension was poored on to water (80 ml), extracted twice with ethyl acetate, dried with sodium sulfate and the solvent was removed. The residue (6.05 g of a dark green oil) was chromatographed on silica gel (eluent: hexane:ethyl acetate::l9:1) to yield Compound 28.5 (3.55 g) which was used in the next step.

Step C: Trans-1-(2'-amino-phenyl)-2-trimethylsilyl-cyclopropane Compound 28.2

Compound 28.5 (3.5 g) was dissolved in methanol (95 ml) and then sodium acetate (1.9 g) and hydroxylamine hydrochloride (1.2 g) were added in sequence. After stirring for 75 minutes at room temperature, the mixture was poured on to sodium hydroxide (500 ml, 0.1N in water) and extracted twice with ethyl acetate. Work-up as described in Step B and chromatography of the semi solid residue (3.8 g) on silica gel (eluent: hexane:ethyl acetate: 9:1) gave Compound 28.2 (1.9 g) as an oil.

Step D: Compound 5.3

This compound was prepared from trans-1-(2'-amino-phenyl)-2-trimethylsilyl-cyclopropane [Compound 28.2] (0.25 g) and 2-methyl-4-trifluoromethyl-4-chlorocarbonyl-thiazole (0.28 g) as described in Example 1 step C. The yield was 0.45 g of off-white crystals melting at.61-64° C.

EXAMPLE 4

This Example illustrates the preparation of Compound Number 3.3.

N-Methyl-4-trifluormethyl-3- pyrrole carboxylic acid (0.24 g), Compound 28.2 (0.25 g) and triethyl amine (0.34 ml) were dissolved in dry dichloromethane (25 ml), cooled with ice and treated with bis-(2-oxo-3oxazolidinyl-phosphinic acid chloride (0.31 g). The resultant suspension was stirred for 1 hour in an icebath and for 15 hours at room temperature. Then the mixture was diluted with ethyl acetate (250 ml) and then saturated sodium bicarbonate solution (125 ml) was added. The organic phase was separated and dried with sodium sulfate. Removal of the solvent and chromatography of the residue (0.45 g of a yellow oil) on silica gel (eluent: hexane:ethyl acetate::2:1) yielded Compound 2.3 (0.2 g) as an oil.

EXAMPLE 5

This Example illustrates the preparation of Compound Number 1.84.

2-Amino-(4' trimethylsilylethinyl)biphenyl, was prepared from 2-amino-4'-bromobiphenyl in analogy to the method described by Sonagashira (Synthesis 1980, 627). This compound was reacted with N-methyl-3-trifluoromethyl-4-chlorocarbonyl-pyrazole in an analogous manner to that described in Example 1 Step C to yield an amide (m.p.151-153° C.). This amide (0.5 g) was then dissolved in THF (10 ml) and was then hydrogenated over Pd (0.1 g; 10% on carbon) at room temperature and atmospheric pressure. The reaction mixture was filtered to remove the catalyst and the solvent was evaporated. The residue (0.52 g of off-white crystals) was chromatographed on silica gel (eluent: hexane: ethyl acetate::2:1) to yield Compound 1.84 (0.43 g) (mp. 119-121° C.).

EXAMPLE 6

The Example illustrates the preparation of Compound Numbers 1.12 and 1.13.

Compound Number 1.4 (1 g) [prepared in a manner analogous to Example 3 Step D by using N-methyl-3-difluoromethyl-4-chlorocarbonyl pyrazol as coupling partner for Compound Number 28.2] was dissolved in dry THF (50 ml) and sodium hydride (0.13 g as a 55% suspension in mineral oil) were added cautiously. The reaction mixture was stirred at ambient teperature for 2.5 hours. Then propargyl bromide (0.23 g) was added and the reaction mixture was stirred overnight under a nitrogen atmosphere. The resultant suspension was diluted with ethyl acetate (200 ml) and washed with water, dried with sodium sulfate and then the solvent was evaporated. The residue (1.25 g as a yellow oil) was chromatographed on silica gel (solvent: hexane:ethyl acetate 2:1) to yield Compound Number 1.12 (0.47 g) and Compound Number 1.13 (0.52 g), both as light yellow oils.

EXAMPLE 7

The Example illustrates the preparation of the pure enantiomers of Compound Number 1.4.

Racemic Compound Number 1.4 [see example 6 for preparation] (0.1 g per injection) was separated on a preparative chiral HPLC coloumn under the following conditions: coloumn: Chiracel™ OD (Daicel™) 5×50; eluent: n-hexane/2-propanol 70:30; stream: 30 ml/min. After manual separation of the 2 peaks the solvent was evaporated. The residue was taken up in diisopropyl ether anf filtered. Evaporation of the solvent yielded the pure enantiomers; Compound Number 1.4A [specific rotation: −89.1 (c=12.4 g/l)] and Compound Number 1.4B [specific rotation: +87.7 (c=11.1 g/l)], each as a colourless oil.

Formulation Examples for Compounds of Formula (I)

Working procedures for preparing formulations of the compounds of formula I such as Emulsifiable Concentrates, Solutions, Granules, Dusts and Wettable Powders are described in WO97/33890.

Biological Examples: Fungicidal Actions

Example B-1

Action Against *Puccinia recondita*/Wheat (Brownrust on Wheat)

1 week old wheat plants cv. Arina are treated with the formulated test compound (0.02% active ingredient) in a spray chamber. One day after application, the wheat plants are inoculated by spraying a spore suspension ($1\times10^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Infestation is prevented virtually completely (0-5% infestation) with each of Compounds 1.3, 1.4, 1.60a, 1.61a, 1.84, 5.3 and 21.3.

Example B-2

Action Against *Podosphaera leucotricha*/Apple (Powdery Mildew on Apple)

5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Compounds 1.3, 1.4, 1.60a, 1.61a, 1.84, 5.3 and 21.3 each exhibit strong efficacy (<20% infestation).

Example B-3

Action Against *Ervsiphe graminis*/Barley (Powdery Mildew on Barley)

1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% r.h. in a greenhouse the disease incidence is assessed.

Compounds 1.3, 1.4, 1.60a, 1.61a, 1.84, 5.3 and 21.3 each exhibit strong efficacy (<20% infestation).

Example B-4

Action Against *Botrytis cinerea*/Tomato (Botrytis on Tomatoes)

4 week old tomato plants cv. Roter Gnom are treated with the formulated test compound (0.02% active ingredient) in a spray chamber. Two days after application, the tomato plants are inoculated by spraying a spore suspension ($1\times10^5$ conidia/ml) on the test plants. After an incubation period of 4 days at 20° C. and 95% r.h. in a growth chamber the disease incidence is assessed.

Compounds 1.3, 1.4, 1.60a, 1.61a and 1.84 each exhibit good efficacy (<50% disease incidence).

Example B-5

Action Against *Altemaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2\times10^5$ conidia/ml) on the test plants. After an incubation period of 3 days at 20° C. and 95% r.h. in a growth chamber the disease incidence is assessed.

Compounds 1.3, 1.4, 1.60a and 1.61a each show good activity in this test (<20% disease incidence).

Example B-6

Action Against *Septoria tritici*/Wheat (*Septoria* Leaf Spot on Wheat)

2 week old wheat plants cv. Riband are treated with the formulated test compound (0.02% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds 1.3, 1.4, 1.60a and 1.61a each show good activity in this test (<20% disease incidence).

Example B-7

Action Against *Uncinula necator*/Rape (Powdery Mildew on Grapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Compounds 1.3, 1.4, 1.60a and 1.61a each show good activity in this test (<20% disease incidence).

Example B-8

Action Against *Venturia inaegualis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4 \times 10^5$ conidia/ml) on the test plants. After an incubation period of 4days at 21° C. and 95% r.h. the plants are placed for 4days at 21° C. and 60% r.h. in a greenhouse. After another 4 day incubation period at 21° C. and 95% r.h. the disease incidence is assessed.

Compounds 1.3, 1.4, 1.60a and 1.61a each exhibit strong efficacy (<20% infestation).

Example B-9

Action Against *Puccinia recondita*/Wheat Apple (Brown Rust on Wheat)

Two days before application, 1 week old wheat plants cv. Arina were inoculated by spraying a spore suspension ($1 \times 10^5$ uredospores/ml) on the test plants. After an incubation period of 1 day at 20° C. and 95% r.h. and for 1 day at 20° C. and 60% r.h. in a greenhouse, the inoculated plants were treated with the formulated test compound in a spray chamber. After an additional incubation period of 8 days at 20° C./18° C. (day/night) and 60% r.h. in a greenhouse the disease incidence was assessed Compounds 1.3, 1.4, 1.60a, 1.61a, 1.84, 5.3 and 21.3 each exhibit strong efficacy (<20% infestation).

The invention claimed is:

1. A compound of formula (I) or an N-oxide thereof:

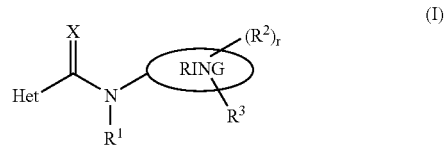

where:
X is O or S;
RING is phenyl or thienyl;
Het is a 5- or 6-membered heterocyclic ring containing one to three heteroatoms, each independently selected from oxygen, nitrogen and sulphur, the ring being substituted by one to four groups $R^4$;
$R^1$ is hydrogen, optionally substituted ($C_{1-4}$)alkyl, formyl, optionally substituted ($C_{1-4}$)alkylC(=O), optionally substituted ($C_{1-4}$)alkylC(=O)O, optionally substituted ($C_{1-4}$)alkoxy($C_{1-4}$)alkyl, optionally substituted allyl, optionally substituted propargyl or optionally substituted allenyl;
each $R^2$ is, independently, halogen, optionally substituted ($C_{1-4}$)alkyl, optionally substituted ($C_{1-4}$)alkoxy or optionally substituted ($C_{1-4}$)alkoxy($C_{1-4}$)alkyl;
$R^3$ is $(CR^aR^b)_m$—Cy—$(CR^cR^d)_n$—Y;
each $R^4$ is, independently, selected from halogen, $C_{1-3}$ alkyl, $C_{1-3}$ haloalkyl, $C_{1-3}$alkoxy($C_{1-3}$)alkyl and cyano;
$R^a$, $R^b$, $R^c$ and $R^d$ are each, independently, hydrogen or optionally substituted ($C_{1-4}$)alkyl;
Cy is an optionally substituted carbocyclic or heterocyclic 3-7 membered ring which may be saturated, unsaturated or aromatic and which optionally contains a silicon atom as a ring member; $(CR^aR^b)_m$ and $(CR^cR^d)_n$ may be bound either to the same carbon or silicon atom of Cy or to different atoms separated by 1, 2 or 3 ring members;
Y is $Si(O_pZ^1)(O_qZ^2)(O_sZ)$ and provided that Cy contains a silicon atom as a ring member then Y may also be hydrogen;
Z is $C_{1-4}$ alkyl or $C_{2-4}$ alkenyl each of which is optionally interrupted by one heteroatom selected from O, S and N and is optionally substituted by one to three independently selected halogen atoms;
$Z^1$ and $Z^2$ are, independently, methyl or ethyl;
m and n are each, independently, 0, 1, 2 or 3;
p, q and s are each, independently, 0 or 1; and
r is 0, 1 or 2;
provided that Y is not tri($C_{1-4}$)alkylsilyl when m and n are both 0 and RING and Cy are both phenyl.

2. A compound as claimed in claim 1 where X is oxygen.

3. A compound as claimed in claim 1 where Het is pyrazolyl, pyrrolyl, thiophenyl, furyl, thiazolyl, isothiazolyl, oxazolyl, isoxazolyl, triazolyl, pyridinyl, pyrazinyl, pyrimidinyl, pyridazinyl, 5,6-dihydropyranyl or 5,6-dihydro-1,4-oxathiinyl each being substituted by one to three groups $R^4$ and connected to the group C(=X)—N($R^1$) via a carbon atom.

4. A compound as claimed in claim 1, where $R^1$ is hydrogen, propargyl, allenyl, formyl, $CH_3C$(=O), $C_2H_5C$(=O) or $CH_3OCH_2C$(=O).

5. A compound as claimed in claim 1, where each $R^2$ is, independently, selected from halogen, methyl, trifluoromethyl and trifluoromethoxy.

6. A compound as claimed in claim 1, where $(CR^aR^b)_m$—Cy—$(CR^cR^d)_n$—Y is attached to the "RING" at a carbon ortho to the carbon which carries the $N(R^1)C(=X)$Het group.

7. A compound as claimed in claim 1, where r is 0 or 1.

8. A composition for controlling microorganisms attack and infestation of plants therewith, comprising the compound as claimed in claim 1 together with a suitable carrier.

9. A method of controlling infestation of cultivated plants by phytopathogenic microorganisms by applying the compound as claimed in claim 1 or the composition as claimed in claim 8 to plants, to parts thereof or to locus thereof.

* * * * *

UNITED STATES PATENT AND TRADEMARK OFFICE
CERTIFICATE OF CORRECTION

PATENT NO. : 7,618,952 B2  Page 1 of 1
APPLICATION NO. : 10/569343
DATED : November 17, 2009
INVENTOR(S) : Ehrenfreund et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 659 days.

Signed and Sealed this

Twenty-sixth Day of October, 2010

David J. Kappos
*Director of the United States Patent and Trademark Office*